United States Patent
Nortman et al.

(10) Patent No.: US 11,877,812 B2
(45) Date of Patent: Jan. 23, 2024

(54) SYSTEM AND METHOD FOR PREPARING BONE

(71) Applicant: MAKO Surgical Corp., Weston, FL (US)

(72) Inventors: Scott David Nortman, Sunrise, FL (US); Amit Mistry, Plantation, FL (US); Jason K. Otto, Plantation, FL (US); Robert Van Vorhis, Davis, CA (US); Mark Ellsworth Nadzadi, Memphis, TN (US); Miranda Jamieson, Fort Lauderdale, FL (US)

(73) Assignee: MAKO Surgical Corp., Weston, FL (US)

(*) Notice: Subject to any disclaimer, the term of this patent is extended or adjusted under 35 U.S.C. 154(b) by 413 days.

(21) Appl. No.: 17/334,092

(22) Filed: May 28, 2021

(65) Prior Publication Data

US 2021/0282872 A1  Sep. 16, 2021

Related U.S. Application Data

(60) Continuation of application No. 16/148,624, filed on Oct. 1, 2018, now Pat. No. 11,065,067, which is a
(Continued)

(51) Int. Cl.
*A61B 34/00* (2016.01)
*A61F 2/30* (2006.01)
(Continued)

(52) U.S. Cl.
CPC .............. *A61B 34/25* (2016.02); *A61B 34/30* (2016.02); *A61F 2/30771* (2013.01); *A61F 2/36* (2013.01);
(Continued)

(58) Field of Classification Search
CPC .......... A61B 34/20; A61B 34/25; A61B 34/30
See application file for complete search history.

(56) References Cited

U.S. PATENT DOCUMENTS 4,725,280 A  2/1988 Laure
4,822,362 A  4/1989 Walker et al.
(Continued)

FOREIGN PATENT DOCUMENTS

CH  664686 A5  3/1988
CN  101160104 A  4/2008
(Continued)

OTHER PUBLICATIONS

Canadian Office Action for CA Application No. 2753201 dated Mar. 9, 2016, 3 pages.
(Continued)

*Primary Examiner* — Si Ming Ku
(74) *Attorney, Agent, or Firm* — FOLEY & LARDNER LLP

(57) ABSTRACT

A robotic system for preparing a bone to repair a bone fracture, includes a controllable guide structure configured to guide preparation of at least one bone piece during execution of a surgical plan and a control system configured to define the surgical plan. Defining the surgical plan includes determining a desired relationship between at least a first bone piece and a second bone piece that are separated by the bone fracture and planning preparation of the first bone piece to include a prepared anatomical structure configured to align the first bone piece with the second bone piece such that when aligned, the first bone piece and the second bone piece will achieve the desired relationship. The control system is further configured to control the controllable guide structure according to the surgical plan.

26 Claims, 29 Drawing Sheets

Related U.S. Application Data continuation of application No. 14/201,404, filed on Mar. 7, 2014, now Pat. No. 10,085,804, which is a division of application No. 12/711,137, filed on Feb. 23, 2010, now abandoned.

(60) Provisional application No. 61/208,451, filed on Feb. 24, 2009.

(51) Int. Cl.
| | |
|---|---|
| *A61F 2/36* | (2006.01) |
| *A61F 2/38* | (2006.01) |
| *A61B 34/30* | (2016.01) |
| A61B 17/17 | (2006.01) |
| A61F 2/34 | (2006.01) |
| A61F 2/46 | (2006.01) |
| A61B 90/00 | (2016.01) |

(52) U.S. Cl.
CPC .............. *A61F 2/38* (2013.01); *A61B 17/175* (2013.01); *A61B 17/1746* (2013.01); *A61B 17/1764* (2013.01); *A61B 90/39* (2016.02); *A61F 2/30724* (2013.01); *A61F 2002/30795* (2013.01); *A61F 2002/30805* (2013.01); *A61F 2002/30823* (2013.01); *A61F 2002/30878* (2013.01); *A61F 2002/30883* (2013.01); *A61F 2002/3412* (2013.01); *A61F 2002/3895* (2013.01); *A61F 2002/4631* (2013.01)

(56) References Cited

U.S. PATENT DOCUMENTS

| | | |
|---|---|---|
| 4,919,671 A | 4/1990 | Karpf |
| 4,957,510 A | 9/1990 | Cremascoli |
| 4,979,949 A | 12/1990 | Matsen et al. |
| 5,198,308 A | 3/1993 | Shetty et al. |
| 5,207,680 A | 5/1993 | Dietz et al. |
| 5,344,423 A | 9/1994 | Dietz et al. |
| 5,408,409 A | 4/1995 | Glassman et al. |
| 5,474,559 A | 12/1995 | Bertin et al. |
| 5,486,180 A | 1/1996 | Dietz et al. |
| 5,549,697 A | 8/1996 | Caldarise |
| 5,560,096 A | 10/1996 | Stephens |
| 5,593,411 A | 1/1997 | Stalcup et al. |
| 5,601,563 A | 2/1997 | Burke et al. |
| 5,634,927 A | 6/1997 | Houston et al. |
| 5,766,256 A | 6/1998 | Oudard et al. |
| 5,776,136 A | 7/1998 | Sahay et al. |
| 5,853,415 A | 12/1998 | Bertin et al. |
| 6,102,954 A | 8/2000 | Albrektsson et al. |
| 6,217,617 B1 | 4/2001 | Bonutti |
| 6,379,388 B1 | 4/2002 | Ensign et al. |
| 6,540,786 B2 | 4/2003 | Chibrac et al. |
| 6,554,838 B2 | 4/2003 | McGovern et al. |
| 6,676,669 B2 | 1/2004 | Charles et al. |
| 6,702,805 B1 | 3/2004 | Stuart |
| 6,723,106 B1 | 4/2004 | Charles et al. |
| 7,179,295 B2 | 2/2007 | Kovacevic |
| 7,338,526 B2 | 3/2008 | Steinberg |
| 7,458,991 B2 | 12/2008 | Wang et al. |
| 7,537,664 B2 | 5/2009 | O'Neill et al. |
| 7,572,293 B2 | 8/2009 | Rhodes et al. |
| 7,674,426 B2 | 3/2010 | Grohowski, Jr. |
| 7,695,519 B2 | 4/2010 | Collazo |
| 7,819,919 B2 | 10/2010 | Fell |
| 7,862,619 B2 | 1/2011 | Clark |
| 7,867,236 B2 | 1/2011 | Hodorek et al. |
| 7,892,243 B2 | 2/2011 | Stuart |
| 7,896,923 B2 | 3/2011 | Blackwell et al. |
| 7,927,335 B2 | 4/2011 | Deffenbaugh et al. |
| 7,998,205 B2 | 8/2011 | Hagen et al. |
| 8,100,981 B2 | 1/2012 | Clark et al. |
| 8,211,113 B2 | 7/2012 | Brown et al. |
| 8,506,645 B2 | 8/2013 | Blaylock et al. |
| 8,535,385 B2 | 9/2013 | Hanssen et al. |
| 8,556,908 B2 | 10/2013 | Nycz et al. |
| 8,562,608 B2 | 10/2013 | May et al. |
| 8,753,401 B2 | 6/2014 | Dee |
| 8,764,760 B2 | 7/2014 | Metzger et al. |
| 8,764,839 B2 | 7/2014 | Rhodes et al. |
| 8,852,195 B2 | 10/2014 | Justin et al. |
| 8,945,222 B2 | 2/2015 | Linares |
| 9,138,259 B2 | 9/2015 | Maxson et al. |
| 9,173,666 B2 | 11/2015 | Metzger et al. |
| 9,579,216 B2 | 2/2017 | Axelson et al. |
| 2002/0022889 A1 | 2/2002 | Chibrac et al. |
| 2002/0107573 A1 | 8/2002 | Steinberg |
| 2002/0183760 A1 | 12/2002 | McGovern et al. |
| 2003/0014122 A1 | 1/2003 | Whiteside |
| 2003/0028196 A1 | 2/2003 | Bonutti |
| 2003/0100953 A1 | 5/2003 | Rosa et al. |
| 2003/0130665 A1 | 7/2003 | Pinczewski et al. |
| 2004/0193280 A1 | 9/2004 | Webster et al. |
| 2005/0085915 A1 | 4/2005 | Steinberg |
| 2005/0143831 A1 | 6/2005 | Justin et al. |
| 2005/0192588 A1 | 9/2005 | Garcia |
| 2006/0009853 A1 | 1/2006 | Justin et al. |
| 2006/0052875 A1 | 3/2006 | Bernero et al. |
| 2006/0089621 A1 | 4/2006 | Fard |
| 2006/0089646 A1* | 4/2006 | Bonutti ............... A61L 27/3834 606/279 |
| 2006/0095135 A1 | 5/2006 | Kovacevic |
| 2006/0147332 A1 | 7/2006 | Jones et al. |
| 2006/0228247 A1 | 10/2006 | Grohowski |
| 2007/0005142 A1 | 1/2007 | Rhodes et al. |
| 2007/0100462 A1 | 5/2007 | Lang et al. |
| 2007/0270685 A1 | 11/2007 | Kang et al. |
| 2007/0299530 A1 | 12/2007 | Rhodes et al. |
| 2007/0299532 A1* | 12/2007 | Rhodes ................ A61F 2/389 623/20.32 |
| 2008/0154270 A1 | 6/2008 | Haines et al. |
| 2008/0202274 A1 | 8/2008 | Stuart |
| 2008/0275452 A1 | 11/2008 | Lang et al. |
| 2009/0000626 A1 | 1/2009 | Quaid et al. |
| 2009/0076605 A1 | 3/2009 | Linares |
| 2009/0198340 A1 | 8/2009 | Cloutier et al. |
| 2009/0270995 A1 | 10/2009 | Rhodes et al. |
| 2009/0287222 A1* | 11/2009 | Lee .................... A61B 17/1633 128/898 |
| 2010/0076441 A1 | 3/2010 | May et al. |
| 2010/0082034 A1 | 4/2010 | Remia |
| 2010/0145343 A1 | 6/2010 | Johnson et al. |

FOREIGN PATENT DOCUMENTS

| | | |
|---|---|---|
| DE | 30 06 178 A1 | 7/1981 |
| DE | 39 17 285 A1 | 11/1990 |
| DE | 43 04 022 A1 | 8/1994 |
| DE | 19723620 A1 | 12/1998 |
| EP | 0 151 724 A1 | 8/1985 |
| EP | 0 349 173 A1 | 1/1990 |
| EP | 0 450 121 A1 | 10/1991 |
| EP | 1 136 046 A2 | 9/2001 |
| FR | 2738739 A1 | 3/1997 |
| WO | WO-85/02535 A1 | 6/1985 |
| WO | WO-95/14444 A1 | 6/1995 |
| WO | WO-2007/029276 A2 | 3/2007 |

OTHER PUBLICATIONS

Communication Pursuant to Article 94(3) EPC for EP Application No. 10 706 434.7, dated Jan. 23, 2015, 5 pages.
Communication Pursuant to Article 94(3) EPC for EP Application No. 10 706 434.7, dated Jun. 7, 2013, 5 pages.
Communication pursuant to Article 94(3) for EP Application No. 15177893.3, dated May 22, 2019, 5 pages.
Extended European Search Report for EP Application No. 15177893.3 dated Jan. 15, 2016, 7 pages.
International Search Report and Written Opinion dated Sep. 20, 2010 mailed in PCT/US2010/025098.

(56) References Cited

OTHER PUBLICATIONS

Invitation to Pay Additional Fees and Partial International Search Report dated Jul. 1, 2010 for International Application No. PCT/US2010/025098.

* cited by examiner

SYSTEM AND METHOD FOR PREPARING BONE

CROSS-REFERENCE TO RELATED PATENT APPLICATIONS

This application is a continuation of U.S. patent application Ser. No. 16/148,624, filed on Oct. 1, 2018, which is a continuation of U.S. patent application Ser. No. 14/201,404, filed on Mar. 7, 2014, which is a divisional of U.S. patent application Ser. No. 12/711,137, filed on Feb. 23, 2010, which claims the benefit of U.S. Provisional Application No. 61/208,451, filed on Feb. 24, 2009, each of which is hereby incorporated by reference in its entirety.

BACKGROUND OF THE INVENTION

The present invention relates to a prosthetic device for implantation in bone, methods of planning bone removal for implantation of a prosthetic device in bone, and robotic systems for preparing a bone to receive a prosthetic device.

Conventional prosthetic implantation techniques involve resecting a pocket of material from a bone to provide a void or pocket within the bone that receives a prosthetic device. After resection of bone material is complete, the prosthetic device is implanted within the pocket. The prosthetic device is typically secured in place with bone cement.

Using the conventional techniques, undesired movement of the prosthetic device relative to the bone may occur. In particular, the pocket in the bone often includes an expansion gap that provides empty space between the prosthetic device and the remaining bone. This expansion gap may be filled or partially filled with bone cement during implantation of the prosthetic device to permit uniform or near uniform dispersion of the bone cement. FIG. 34 shows a top view of an example of a conventional prosthetic device 10 implanted in a medial condyle 12 of a tibia (the lateral condyle 14 is shown for reference). An expansion gap 16 is provided between the prosthetic device 10 and an edge of the remaining bone in the medial condyle. The expansion gap, which is typically 0.5-0.8 mm in a tibia, is exaggerated in this drawing for purposes of illustration. This expansion gap may cause the prosthetic device to be less than fully constrained, which can permit unwanted movement of the prosthetic device. Consequently, the prosthetic device may move (e.g., rotate or translate) relative to the bone when a force is applied to the prosthetic device. For example, during trial articulation of a leg, contact forces from a femoral condyle can cause unwanted movement of a tibial inlay. In addition, undesired movement can occur during final fixation as a surgeon presses against the prosthetic device to disperse the bone cement and squeeze out excess bone cement.

Using conventional techniques, it also may be undesirably difficult to properly position a prosthetic device in the pocket in the bone. For example, there can be difficulty in positioning the cup of a hip acetabulum in a desired tilt/abduction and anteversion due to difficulty in knowing exactly where a pelvis is located during total hip arthroplasty.

SUMMARY

An embodiment relates to prosthetic device for implantation in bone. The prosthetic device includes a body portion for attachment to a bone, wherein the body portion includes an implantation surface configured to face the bone upon implantation. The prosthetic device further includes constraint structure comprising at least one of: (i) at least one compressive projection projecting from the implantation surface in a lateral direction of the body portion and configured to provide a compressive force between the at least one compressive projection and the bone, (ii) at least one interlock projection projecting from the implantation surface and having an interlock-projection surface configured to receive bone in a space between the interlock-projection surface and a proximal portion of the implantation surface, and (iii) at least one recess in the implantation surface and configured to receive bone to constrain the body portion in at least two translational degrees of freedom. The constraint structure is configured to constrain the prosthetic device in the bone.

Another embodiment relates to a method for planning bone removal for implantation of a prosthetic device into bone. The method includes storing data representative of a prosthetic device in a computer readable medium, wherein the prosthetic device includes a body portion having an implantation surface configured to face the bone upon implantation and at least one feature that provides a constraint structure that will constrain the prosthetic device in the bone. The method further includes defining, based on the data, at least one bone-cutting pattern for (i) removing a first portion of bone in a first area sufficient to seat the body portion and (ii) at least one of removing and maintaining a second portion of bone in a second area configured to interact with the constraint structure.

Yet another embodiment relates to a robotic system for preparing a bone to receive a prosthetic device. The robotic system includes a controllable guide structure configured to guide cutting of the bone into a shape for receiving the prosthetic device. The robotic system further includes a computer readable medium for storing data representative of the prosthetic device, wherein the prosthetic device includes a body portion having an implantation surface configured to face the bone upon implantation and at least one feature that provides a constraint structure that will constrain the prosthetic device in the bone. The robotic system further includes a control system for controlling the guide structure, wherein the control system is configured to define at least one bone-cutting pattern for (i) removing a first portion of bone in a first area sufficient to seat the body portion and (ii) at least one of removing and maintaining a second portion of bone in a second area configured to interact with the constraint structure.

BRIEF DESCRIPTION OF THE FIGURES

The accompanying drawings, which are incorporated and constitute a part of this specification, illustrate embodiments of the invention and together with the description serve to explain aspects of the invention.

FIG. 5b is a perspective view of a tibia having the pocket of FIG. 5a.

FIG. 6b is a top view of the projection of FIG. 6a.

FIG. 6c is a side view of the projection of FIG. 6a.

FIG. 6d is a front view of the projection of FIG. 6a.

FIG. 18b is a cross sectional view taken along line B-B in FIG. 18a.

FIG. 20 is a cross-sectional view of the prosthetic device of FIG. 19a.

FIG. 21b is a side cross sectional view of the femur of FIG. 21a.

FIG. 22 is a perspective view of a prosthetic device for implanting in the pocket of FIG. 21a.

FIG. 26b is a top view of the prosthetic device of FIG. 26a.

DETAILED DESCRIPTION OF PREFERRED EMBODIMENTS

Figure 1:
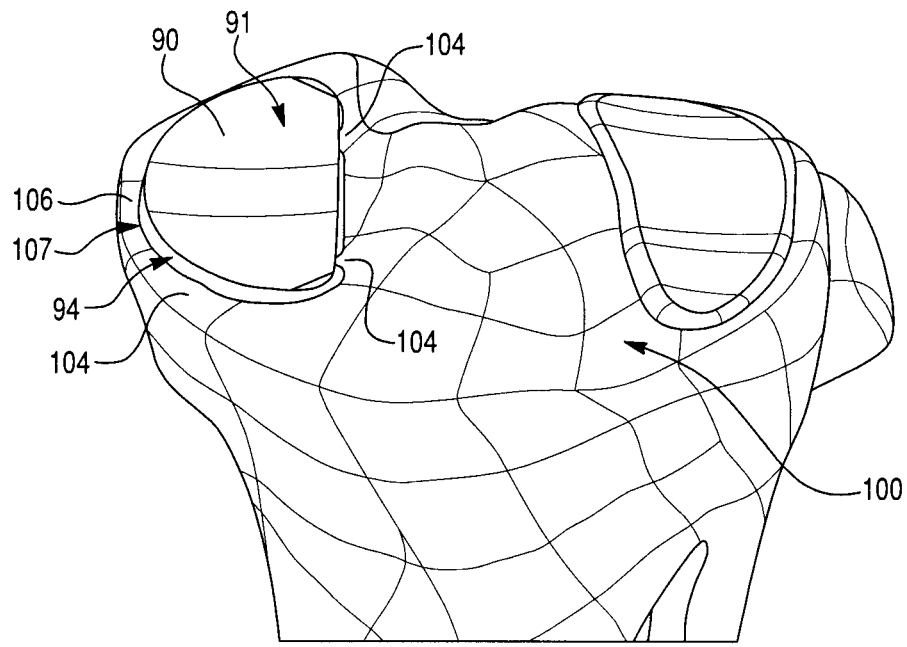
FIG. 1 is a perspective view of a prosthetic device implanted in a pocket in a tibia, according to an embodiment.

Presently preferred embodiments of the invention are illustrated in the drawings. An effort has been made to use the same or like reference numbers throughout the drawings to refer to the same or like parts.

Overview

The preferred embodiments relate, in general, to methods for planning bone removal to allow implantation of a prosthetic device to create a constraining relationship between the bone and the prosthetic device. The preferred embodiments also relate to prosthetic devices that are configured to achieve such a constraining relationship and a robotic system that can be used to facilitate the creation of such a constraining relationship.

In general, the methods for planning include storing data representative of the prosthetic device in a computer readable medium. The methods further include defining, based on the data, at least one bone-cutting pattern for (i) removing a first portion of bone in a first area sufficient to seat a body portion of the prosthetic device and (ii) at least one of removing and maintaining a second portion of bone in a second area configured to interact with a constraint structure of the prosthetic device. The method also may include displaying information representative of the at least one bone-cutting pattern, for example on a conventional monitor. Particular implementations of the planning methods are described below, though the invention is not limited to those particular implementations.

Particular implementations of prosthetic devices and a robotic system that are useful with the planning methods also are described below. However, the invention is not limited to those particular implementations and the prosthetic devices and robotic system could be used without the planning methods.

Creating Bone Projections that Provide Compressive Force to Prosthetic Device One such implementation of the planning method includes defining the bone cutting pattern for removing a first portion of bone in the first area sufficient to seat a body portion of the prosthetic device and for maintaining a second portion of bone in the second area to provide at least one projection of bone configured to engage an implantation surface of the prosthetic device to provide a compressive force between the projection and implantation surface and constrain the prosthetic device. This compressive force need not be sufficient to deform the projection or the implantation surface, though it may deform one or both.

Figure 2A:
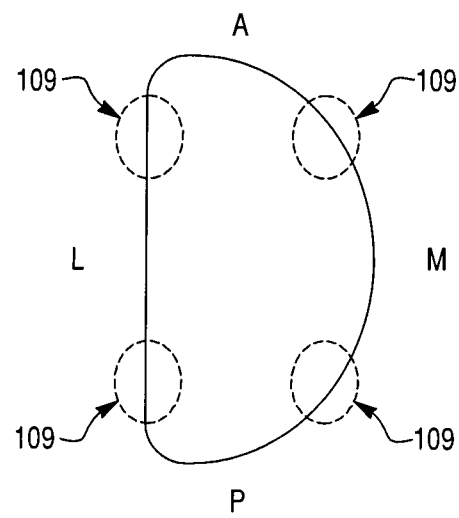
FIG. 2a is a top view of a representation of the pocket and zones where projections are to be provided in bone, according to an embodiment.
Figure 2B:
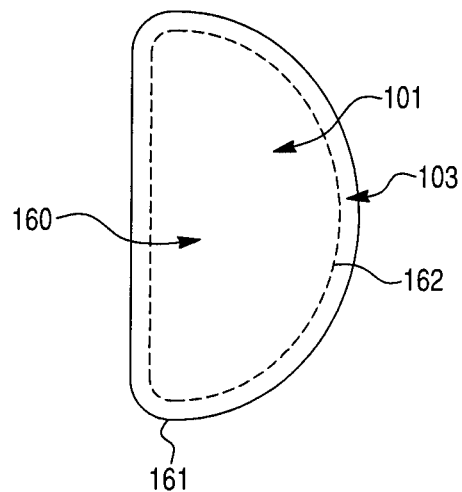
FIG. 2b is a top view of a representation of areas of bone for resection.
Figure 2C:
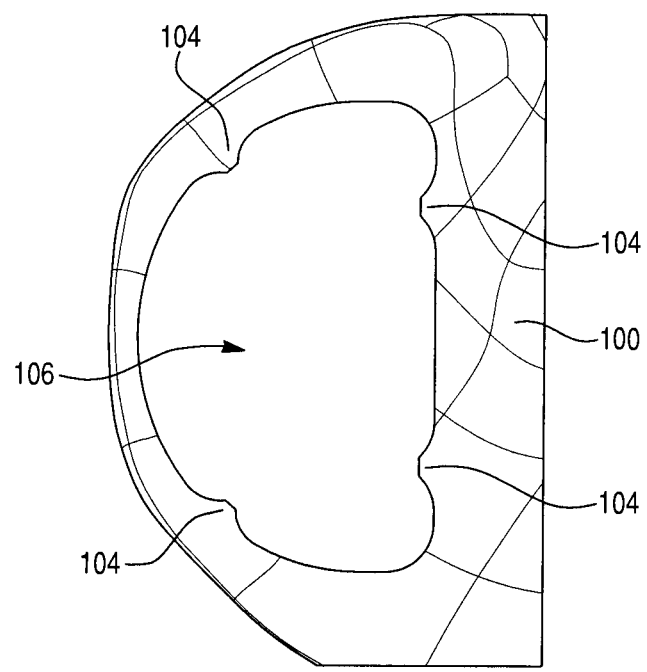
FIG. 2c is a top view of a bone cutting pattern, according to an embodiment.
Figure 2D:
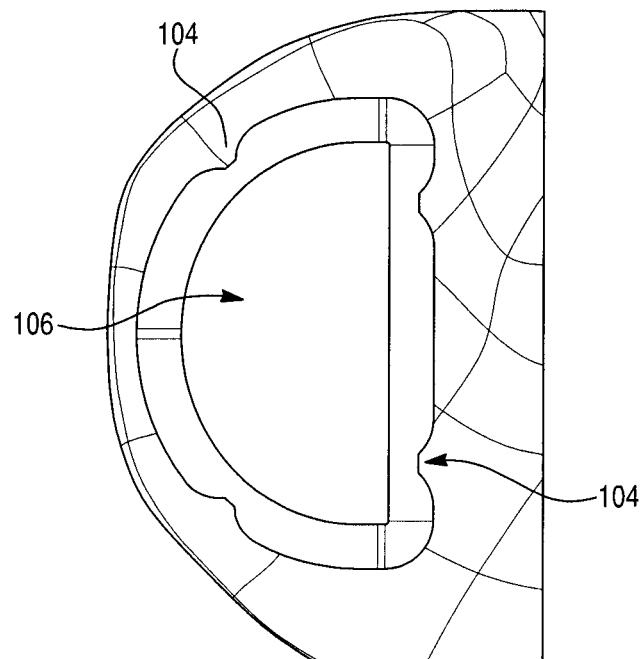
FIG. 2d is a top view of a portion of the tibia of FIG. 1 showing the pocket resected according to the bone cutting pattern of FIG. 2c.
Figure 2E:
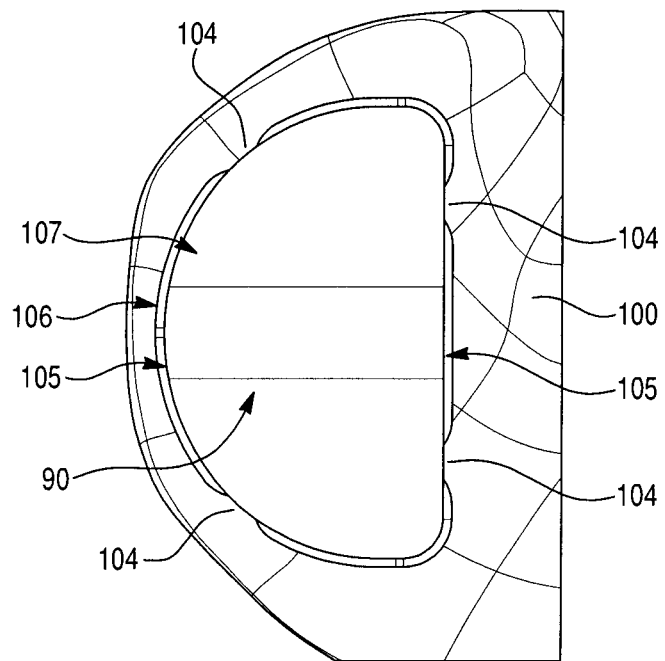
FIG. 2e is a top view of the tibia of FIG. 1 with the prosthetic device in the pocket.

FIGS. 1 and 2e show views of a prosthetic device 90, e.g., a tibial inlay, implanted in a pocket (or bone cavity) 106 formed by resecting bone from a tibia 100 pursuant to such a planning method. The prosthetic device 90 preferably includes a body portion 91 and an implantation surface 94 configured to face the bone of the tibia 100 upon implantation. In this embodiment, the implantation surface 94 can form a constraint structure 107 of the prosthetic device 90. The planning method provides bone projections 104 in the pocket 106 that engage the constraint structure 107 to constrain the prosthetic device 90.

To achieve such a pocket 106 with projections 104, initially zones 109 can be identified in which it is desired to locate the projections 104, as shown in FIG. 2a. In this figure, the anterior A, posterior P, medial M, and lateral L directions are identified. Then, based on data representative of the prosthetic device 90, a bone-cutting pattern is defined for removing a first portion of bone in a first area 101 within line 162 (see FIG. 2b) sufficient to seat the body portion 91 of the prosthetic device 90. The bone-cutting pattern (or another bone cutting pattern) is also defined to remove portions of bone in a second area 103 (between lines 161 and 162) while maintaining second portions of bone to provide the projections 104 that are configured to interact with the constraint structure 107 of the prosthetic device 90.

The resulting bone cutting pattern (or patterns) is shown in FIG. 2c. This bone cutting pattern is designed to provide the pocket 106 with the projections 104 extending toward the center of the pocket 106. Bone resection can then be carried out based on this bone cutting pattern to achieve the pocket 106 with projections 104, as shown in FIG. 2d.

As shown in FIG. 2e, the prosthetic device 90 can then be disposed in the pocket 106. The projections 104 preferably engage the prosthetic device 90 such that a compressive force is provided between the prosthetic device 90 and the projections 104 such that the location and position of the prosthetic device 90 can be established in the tibia 100 with a relatively high degree of accuracy and precision. The projections can be provided to minimize or prevent unwanted movement of a prosthetic device, such as unwanted translation or rotation of a prosthetic device. Furthermore, the projections can provide real-time cues to a practitioner when a trial or final prosthetic device is in place, such as audial, visual, or tactile cues.

Due to the engagement of a prosthetic device with the projections when the prosthetic device is inserted into a location into bone, an audible sound can be produced, similar to a part "snapping" into place, the engagement between the prosthetic device and the bone can be visually checked, and a practitioner can feel how snugly the engagement between the prosthetic device and the projections is. Thus, configuration of the prosthetic device and the engagement of the prosthetic device with the projections provides a practitioner with enhanced confidence that the prosthetic device has been located and positioned closely to a surgical plan.

Such a pocket 106 can be formed to accommodate bone cement or other joining substance (referred to generally as adhesive). In particular, an expansion gap 105 can be maintained between the prosthetic device 90 and the surface of the tibia 100 so that the adhesive can flow into the expansion gap 105 to partially or fully fill the expansion gap 105 to assist in the fixation of the prosthetic device 90 to the tibia 100.

The size and location of the projections 104 can be controlled to provide optimal location and positioning of a prosthetic device. As shown in the examples of FIGS. 1-2*e*, a tibia 100 preferably is prepared to provide four projections 104.

Figure 3A:
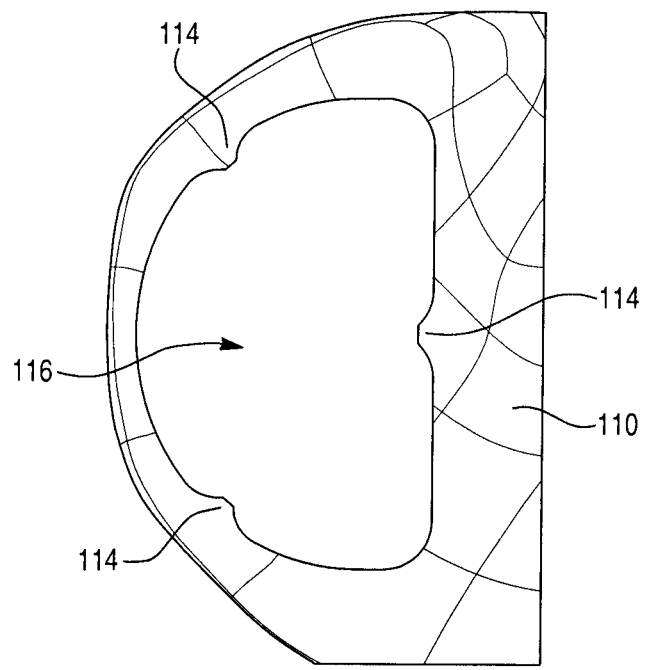
FIG. 3a is a top view of a portion of a tibia showing an intended pocket with three projections, according to an embodiment.
Figure 3B:
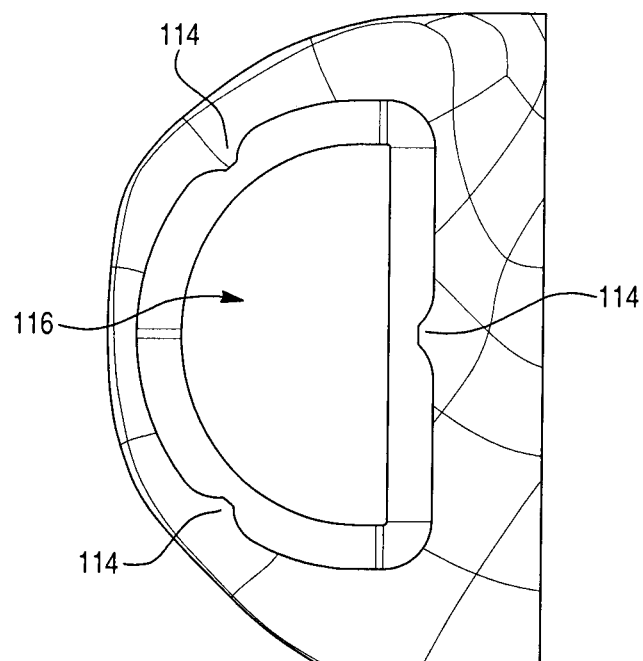
FIG. 3b is a top view of the tibia of FIG. 3a, showing the pocket without the prosthetic device.
Figure 3C:
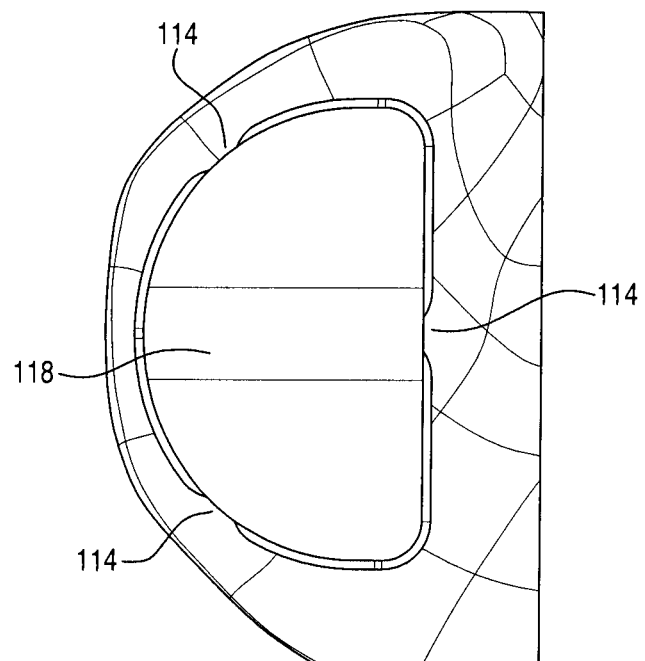
FIG. 3c is a top view of the tibia of FIG. 3a with the prosthetic device in the pocket.

However, fewer projections can be provided. FIGS. 3*a*-3*c* show an embodiment of a portion of a tibia 110 that has been prepared by resecting bone to provide a pocket 116 that receives a prosthetic device in a similar manner as the previous embodiment. The embodiment of FIGS. 3*a*-3*c* has only three bone projections 114 that can engage with a prosthetic device 118 instead of four bone projections.

The bone projections 104, 114 can be provided at various locations to aid in locating and positioning a prosthetic device 90, 118 in the tibia 100, 110. The location of such projections can be selected based upon, for example, the number of the bone projections. For example, a greater number of bone projections can permit a smaller distance between bone projections in relation to an implantation surface of a prosthetic device, such as a circumferential surface of a prosthetic device. Other numbers of bone projections can be provided, such as, for example, five, six, or more bone projections, which can be selected to affect the distribution of compressive forces between a prosthetic device and a bone and to affect the amount of expansion gap provided between the prosthetic device and the bone. For example, the number of projections can be selected to provide an advantageous distribution of forces between a prosthetic device and a bone, such as by selecting a greater number of projections and a prosthetic device configured to engage such projections, but a larger-sized expansion gap, which provides enhanced joining of the prosthetic device to a bone via bone cement or other fixation substances, indicates a smaller number of projections. Thus, various considerations must be accounted for when determining which prosthetic device to use and the number and size/shape of projections selected.

Preferably the projections are configured to extend along at least 1% of the circumferential perimeter 161 of the pocket and not more than 75% of the circumferential perimeter 161 (see FIG. 2*b*). Or more particularly, the horizontal length of a prepared anatomical structure can extend between 10% and 50% of the circumferential perimeter 161, or more particularly 20% and 35% of the circumferential perimeter 161.

In addition, the size and location of bone projections can be controlled to affect the compressive force provided between the bone projections and a prosthetic device and to maximize the amount of bone tissue that is preserved. The durability of the bone projections and the prosthetic device can be optimized by controlling the size and location of bone projections. For example, the forces between a prosthetic device and a bone can be distributed and optimized by selecting the configuration of the prosthetic device and the number and/or size of the projections that engage the prosthetic device, thus minimizing or preventing unwanted damage or failure of the prosthetic device or areas of bone, such as the projections.

Bone projections can have various geometries, such as, for example, spheres, cylinders, cones, elliptical tracks, or other geometrical shapes. In another example, the bone projection can essentially form a negative mold of a mating surface of a prosthetic device or a cavity or indentation in bone that substantially matches the shape of a mating surface of a prosthetic device. Such bone projections can be three dimensional or two dimensional in form.

Figure 4:
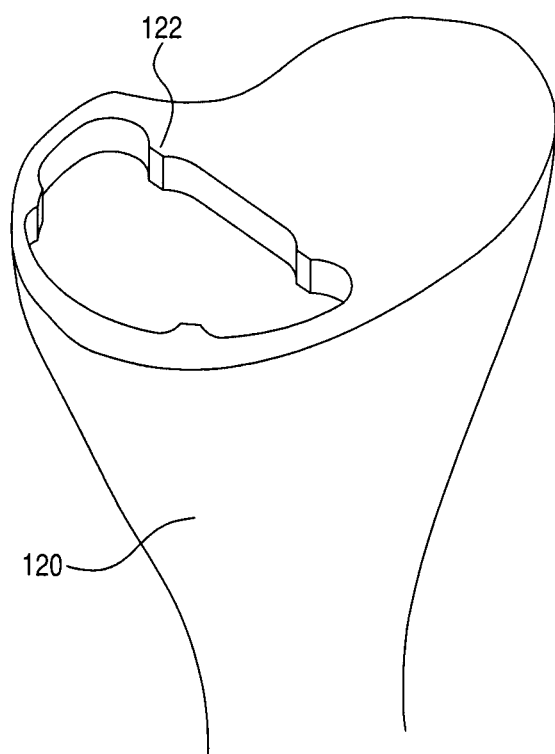
FIG. 4 is a perspective view of a tibia having a pocket with vertically oriented projections, according to an embodiment.
Figure 9:
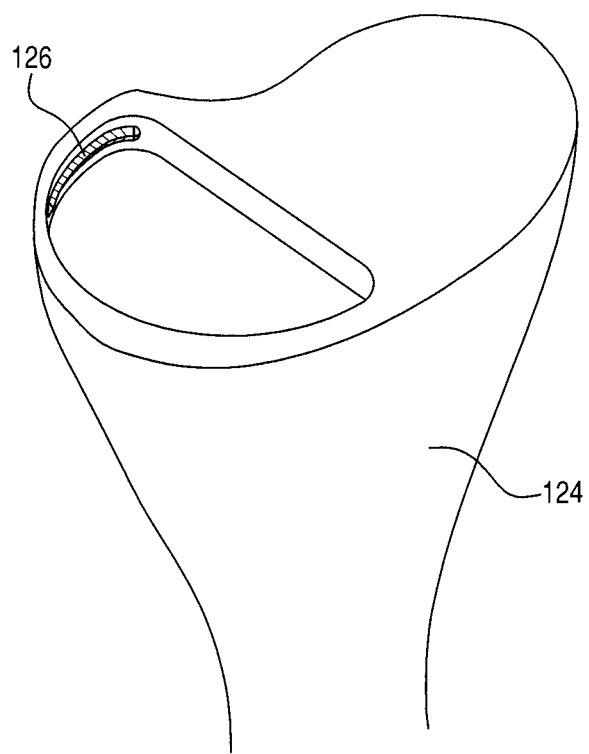
FIG. 9 is a perspective view of a tibia with a horizontally oriented projection, according to an embodiment.

The orientation of bone projections can also be altered to affect the engagement between a prosthetic device and a bone. As shown in the example of FIG. 4, bone projections 122 can be provide in a bone 120 such that the bone projections 122 extend in a vertical direction relative to the bone 120. In another example, bone projections 126 can be prepared in a bone 124 such that the bone projections 126 extend in a substantially horizontal direction relative to the bone 124, as shown in the example of FIG. 9.

In addition, the shape and size of the bone projections can be altered and selected to affect the engagement between a prosthetic device and a bone. The proper size of the bone projections is important not only for the final location and positioning of a prosthetic device but also for the easy insertion and removal of a trial prosthetic device during an implantation procedure so that the constraint of the prosthetic device in a bone may be assessed before final implantation. Further, the selection of the size and shape of the bone projections can affect the location of the bone projections. Thus, the prosthetic devices and methods described herein advantageously assist in the location and positioning of trial prosthetic devices and prosthetic devices that are finally implanted and fixed to bone so that the outcome of a surgical procedure may be even closer to a surgical plan.

Figure 5A:
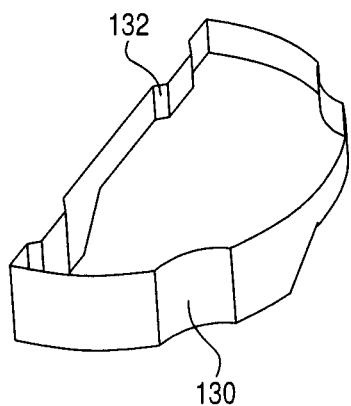
FIG. 5a is a perspective view of a circumferential perimeter of a pocket, according to an embodiment.
Figure 5B:
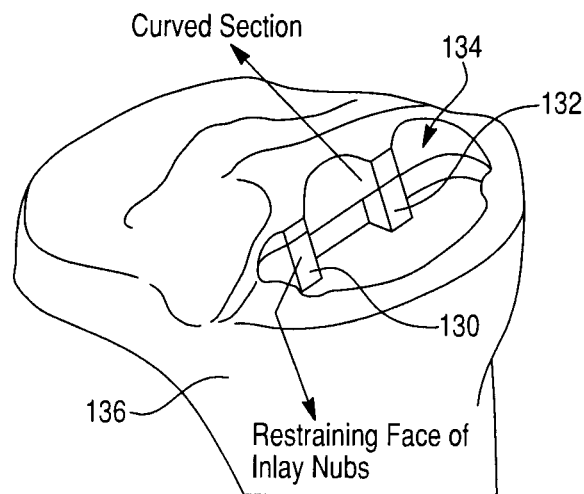
Figure 5C:
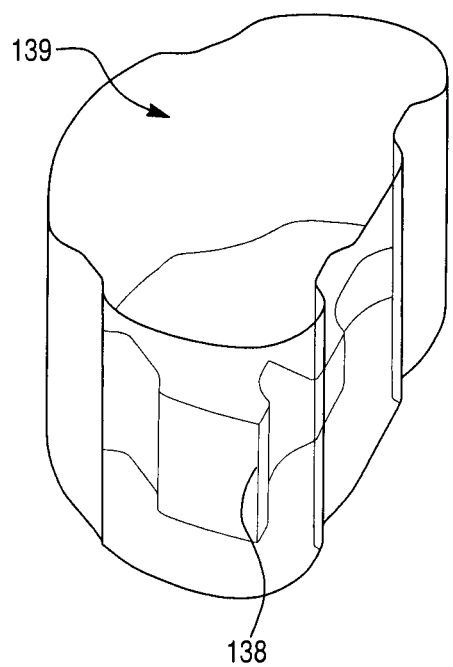
FIG. 5c is a perspective view of a pocket, according to an embodiment.
Figure 5D:
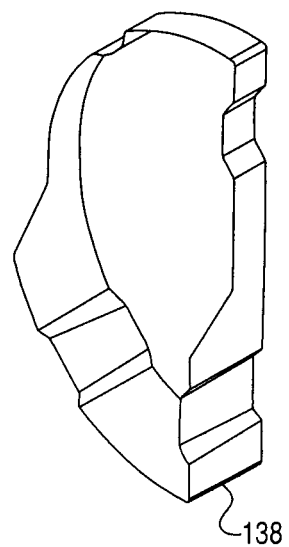
FIG. 5d is a perspective view of the circumferential perimeter of the pocket of FIG. 5c.

FIG. 5*a* shows a perspective view of an exemplary circumferential perimeter of a pocket 134 prepared in a bone 136, as shown the example of FIG. 5*b*. As shown in the example of FIGS. 5*a* and 5*b*, the projections formed from the bone 136 can have a shape that projects into the pocket 134 such that the projections form a constraining face 130 that engages with the features of a prosthetic device. The projections can be shaped to have curved regions 132, such as on lateral sides or edges of the constraining faces 130 of the projections. Such curved regions 132 can be utilized to increase the size of the projections to increase the amount of force the projections may withstand when engaging with a prosthetic device. The shape of the curved region may be selected to avoid sharp corners, which can act as stress risers or multipliers that can lead to damage of projection or joint between a prosthetic device and a bone. In addition, the corners 138 of the pocket can be advantageously shaped to avoid sharp corners and to affect the expansion gap provided between a prosthetic device and the bone, as shown in FIG. 5*c*, which shows a corner within an exemplary pocket 139, and as shown in FIG. 5*d*, which shows the circumferential perimeter of the pocket 139, including a corner 138.

Figure 6A:
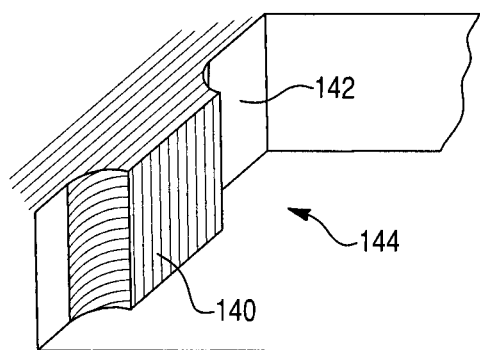
FIG. 6a shows a perspective view of an exemplary projection, according to an embodiment.
Figure 6B:
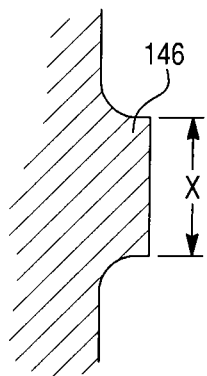
Figure 6C:
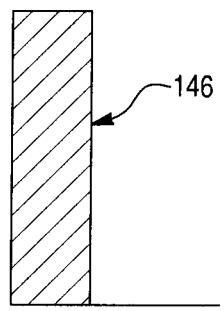
Figure 6D:
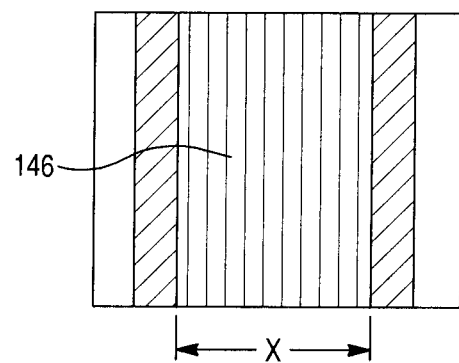

FIG. 6*a* shows a perspective view of an exemplary projection 140 formed on a surface 142 of a bone such that the projection 140 extends into a pocket 144 formed within the bone. FIG. 6*b* shows a top view of the projection of FIG. 6*a*, FIG. 6*c* shows a side view of the projection of FIG. 6*a*, and FIG. 6*d* shows a front view of the projection of FIG. 6*a*. As shown in the examples of FIGS. 6*a*-6*d*, the projection 140 can have a constraint surface 146 that is configured to engage with a prosthetic device. The constraint surface 146 can have a size selected to maximize engagement between a prosthetic device and the projection 140, and thus minimize or prevent unwanted movement of the prosthetic device, but also to provide a properly sized expansion gap between the prosthetic device and the bone to also constrain the prosthetic device. For example, such a constraint surface 146 preferably can have a width X of 1 to 15 mm, 1 to 10 mm, 2 to 8 mm, 2 to 5 mm, 2 to 3 mm, or 2 mm or 3 mm, in order of preference. In another example, the constraint surface can project from the surrounding surface of bone by a distance of 0.01 to 10 mm, 0.1 to 5 mm, 0.25 to 2 mm, 0.5 to 1 mm, in order of preference.

Figure 7A:
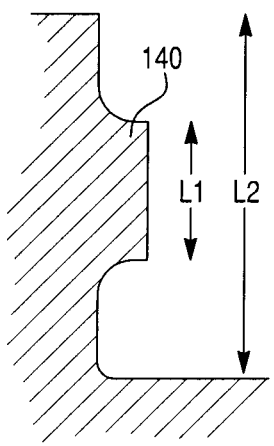
FIG. 7a is a side cross-sectional view of a projection extending only partially along a vertical depth of a pocket, according to an embodiment.
Figure 7B:
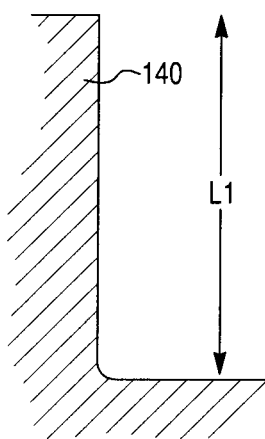
FIG. 7b is a side cross-sectional view of a projection extending 100% of a vertical depth of a pocket, according to an embodiment.

The vertical length of a projection may also be varied to control the engagement between a prosthetic device and bone, the amount of expansion gap, and the amount of bone tissue retained during preparation. As shown in the example of FIG. 7a, a projection 140 can have a vertical height L1 relative to the total depth L2 of a pocket provided within a bone. Such a vertical height L1 of a projection 140 can be expressed as a ratio of the vertical height L1 of the projection 140 to the total depth L2. Projections can be prepared such that the projections have a vertical height ratio of 5 to 100%. FIG. 7b shows an example of a projection 140 with a vertical height L1 that extends 100% of the total depth L2 of a pocket. In another example, projections can have a vertical height ratio of 10 to 90%, 20 to 80%, 25 to 45%, or 40%, in order of preference. Alternatively, the vertical height of a projection can be expressed in terms of a ratio of the vertical height of the projection to a height of a prosthetic device. For example, projections can have a vertical height ratio of 10 to 90%, 20 to 80%, 25 to 45%, or 40%, in order of preference. In another example, each projection can be sized to have a ratio of projection area to total area of 1 to 99%, 5 to 90%, 5 to 80%, 10 to 50%, 15 to 30%, in order of preference.

Figure 8A:
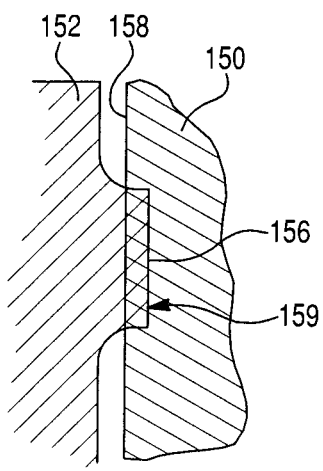
FIG. 8a is a side cross-sectional view showing an interference fit between a prosthetic device and a projection of a bone, according to an embodiment.

The prosthetic device and projections are preferably sized to provide an interference fit or press fit between the constraint features of the prosthetic device and the projections. FIG. 8a shows a side view of an exemplary interference fit between a prosthetic device 150 and a bone 152. Such a prosthetic device 150 can be configured to provide a compliance between the prosthetic device 150 and the bone 152 so that the compressive forces produced between the prosthetic device 150 and the bone 152 may be accommodated by the prosthetic device 150 and the bone 152. Such an interference fit can be created when an implantation surface 158 of a prosthetic device 150 and the surface 156 of a bone, such as at a projection, are oversized such that the surfaces 158, 156 overlap in a spatial region, such as the region 159 indicated in the example of FIG. 8a.

Figure 8B:
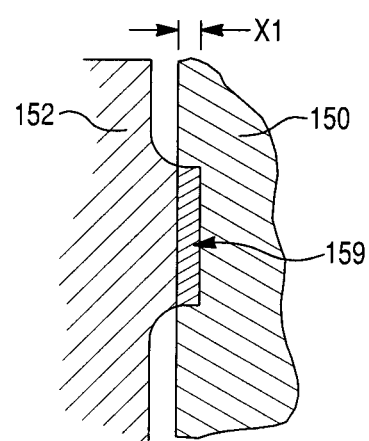
FIG. 8b is a side cross-sectional view showing an interference distance for an interference fit between a prosthetic device and a projection of a bone, according to an embodiment.

As shown in the example of FIG. 8b, the prosthetic device 150 and the bone 152 can overlap in an interference region 159 over a distance Xl, which can be a distance of, for example, 0.25 to 0.75 mm, 0.33 to 0.66 mm, 0.40 to 0.6 mm, or 0.5 mm, in order of preference. Alternatively, a prosthetic device and the prepared anatomical structures of a bone can be configured such that there is an interference fit of 0 mm between the prosthetic device and the bone so that the prosthetic device and bone fit together line to line and substantially without spatial overlap. The surface 156 of a bone 152 can be shaped to accommodate and distribute compressive forces provided between the bone 152 and a prosthetic device 150. For example, the surface 156 of the bone 152 that engages with a prosthetic device 150 can have a rounded or a flat shape.

A prosthetic device and the bone projections can be designed so that compressive forces provided between the prosthetic device and the bone normally remain with a desired range. The following formulas can be utilized when designing a prosthetic device and any prepared anatomical structures:

$$\sigma_A = F/A,$$

$$\sigma_A = E \cdot \varepsilon,$$

where $\sigma_A$ represents a stress applied to a given area, F represents a force applied to that area, A represents the amount of the area, E represents the modulus of the material, and represents an amount of strain induced in the material. The amount of stress induced in a prosthetic device or bone can also be a function of whether a prepared anatomical feature in a bone is a temporary feature, such as a feature used during trials of a prosthetic device, or a permanent prepared anatomical feature. For example, if a prepared anatomical feature is provided as a permanent feature, a prosthetic device and the prepared anatomical feature can be designed such that $\sigma_A$ is less than $\sigma_b$, which represents the yield strength of the bone. In another example, the prosthetic device and the prepared anatomical feature can be designed such that $\sigma_A$ is greater than 0.1 $\sigma_b$ and less than 0.8 $\sigma_b$, or greater than 0.3 $\sigma_b$ and less than 0.7 $\sigma_b$. Conversely, if a prepared anatomical feature of a bone is a temporary feature a prosthetic device and the prepared anatomical feature can be designed such that $\sigma_A$ greater than or equal to $\sigma_b$. More particularly, the prosthetic device and the prepared anatomical feature can be designed such that $\sigma_A$ is less than or equal to 0.5 $\sigma_b$.

The circumferential length prepared anatomical features can be selected to maximize engagement between a prosthetic device and the prepared anatomical features, and thus minimize or prevent unwanted movement of the prosthetic device, but also to provide a properly sized expansion gap between the prosthetic device and a bone to also constrain the prosthetic device with bone cement or another joining substance provided in the expansion gap.

Figure 10:
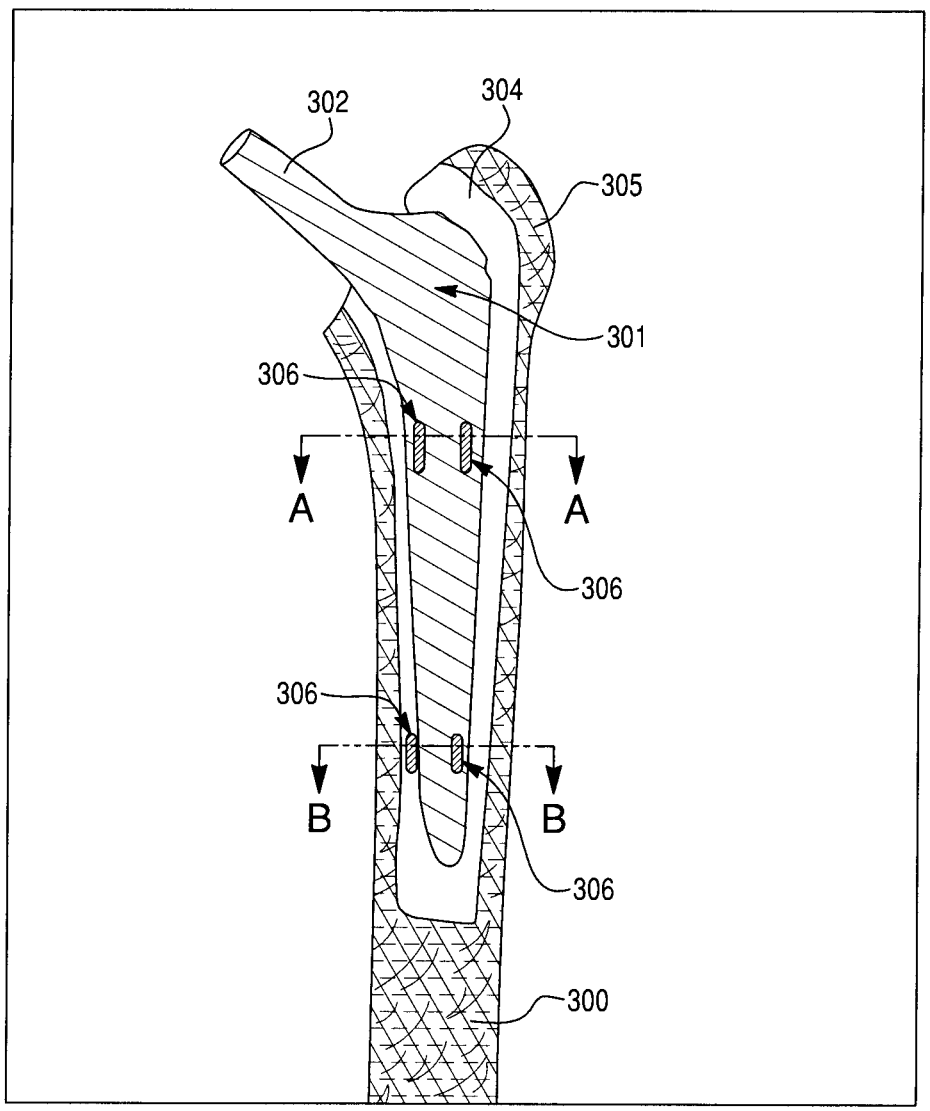
FIG. 10 is a side cross sectional view of a femur with a prosthetic device in a pocket, according to an embodiment.

Although the above examples relate to prosthetic devices for a tibia, the present invention also can be applied to other bones and joints, such as a hip joint. FIG. 10 is a cross sectional view of a femur 300 that has been prepared to provide a pocket for a prosthetic device 302, i.e., a femoral stem, which has been inserted into an opening formed in the cortical bone 305 of the femur 300. The prosthetic device 302 can include a body portion 301. According to another example, the prosthetic device can be a hybrid system that includes a plastic centralizer, although one is not required for the present invention. For example, the prepared anatomical structures of the femur 300 can be sufficient to provide a desired angle for the prosthetic device 302 without additional components or features to provide a varus/valgus angle that is accurate and close to a surgical plan.

The pocket of the femur 300 can be prepared to provide an expansion gap between the prosthetic device 302 and the femur 300 for bone cement 304 or another joining substance. In addition, the femur 300 has been prepared to provide one or more prepared anatomical structures to engage with the prosthetic device 302.

Figure 11A:
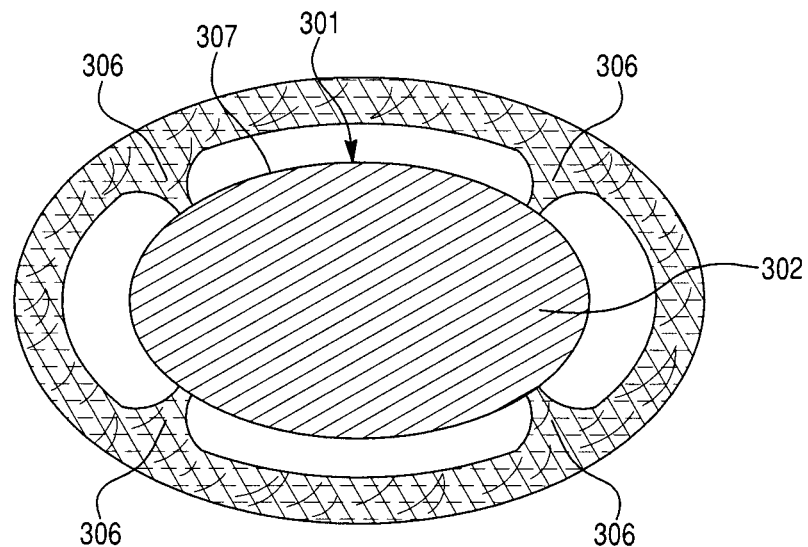
FIG. 11a is a top cross sectional view along line A-A of FIG. 10.
Figure 11B:
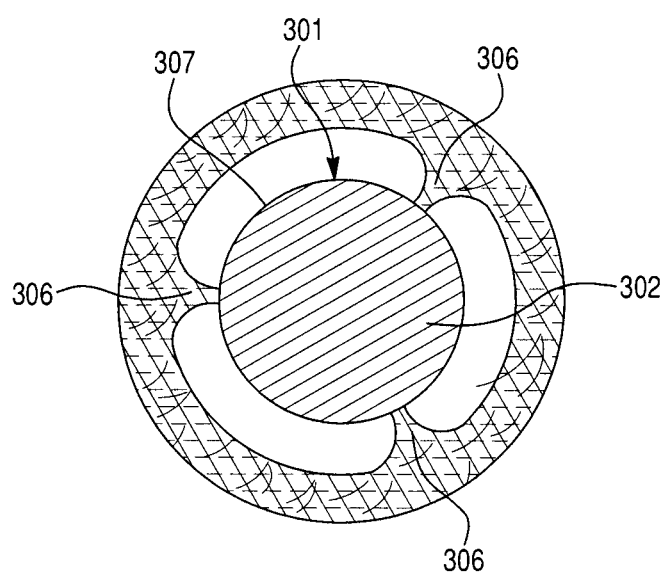
FIG. 11b is a top cross sectional view along line B-B of FIG. 10.

As shown in FIG. 11a, which is a cross sectional view along line A-A in FIG. 10, and in FIG. 11b, which is a cross sectional view along line B-B in FIG. 10, the prepared anatomical structures can be provided as projections 306 that extend from a surface of the femur 300 and engage the prosthetic device 302, such as a constraint structure 307 on an implantation surface 301 of the prosthetic device 302. The projections 306 can be configured to engage with the prosthetic device 302 to provide a compressive force between the projections 306 and the prosthetic device 302. For example, the prosthetic device can include plurality of projections that project from a lateral side portion of an implantation surface of the prosthetic device. According to another example, the projections can extend vertically, as shown in the example of FIGS. 10-11b and/or can extend along a circumferential perimeter of the pocket provided with the femur 300, as discussed in regard to the examples herein. As shown in the examples of FIGS. 11a and 11b, the projections 306 can be provided as three projections or four projections that engage a surface of the prosthetic device 302. In another example, five or more projections can be provided. The projections 306 can be used to center the prosthetic device 302 within the pocket of the femur 300 while providing an expansion gap for the bone cement 304 or other joining substance.

The bone projections described above preferably are permanent, i.e., they remain substantially intact after the prosthetic device has been fully implanted in the pocket. However, it is not required that the bone projections be permanent. They instead could be temporary. For example, the bone projections could be utilized during a particular phase of surgery to position the prosthetic device and thereafter eliminated, e.g., crushed. As a specific example, the bone projections could be used to achieve initial positioning of the prosthetic device and when a surgeon drives the prosthetic device into a final implanted position, such as through an impact force, the bone projections could be configured to be crushed to allow the prosthetic device to move into that final implanted position. As a further alternative, the bone projections could be used to position a trial prosthetic device and then be crushed when the permanent prosthetic device is implanted.

Creating Bone Projections that Project into Recesses in Prosthetic Device

Another implementation of the planning method includes defining the bone cutting pattern for removing a first portion of bone in the first area sufficient to seat a body portion of the prosthetic device and for maintaining a portion of the second portion of bone in the second area to provide a projection that is configured to project into a recess in the prosthetic device forming at least a portion of the constraint structure.

In this embodiment, the pocket in the bone can be formed by a process similar to that described above. However, the bone surface can be prepared to provide projections that interact with a constraint structure, i.e., a recess, of a prosthetic device.

Figure 12A:
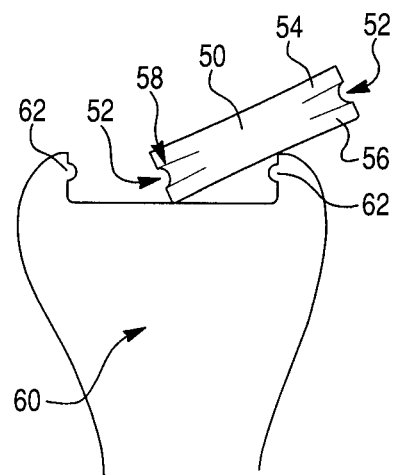
FIG. 12a is a side cross-sectional view of a prosthetic device in a first stage of implantation, according to an embodiment.
Figure 12B:
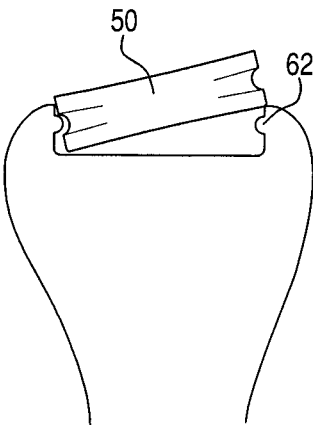
FIG. 12b is a side cross-sectional view of the prosthetic device of FIG. 12a in an advanced stage of implantation.

FIG. 12a shows a cross-sectional view of an exemplary prosthetic device 50 as the prosthetic device 50 is being implanted into a bone 60. FIG. 12b shows the prosthetic device 50 in an advanced stage of implantation into the bone 60, and FIG. 12c shows the prosthetic device 50 after implantation into the bone 60.

Figure 12C:
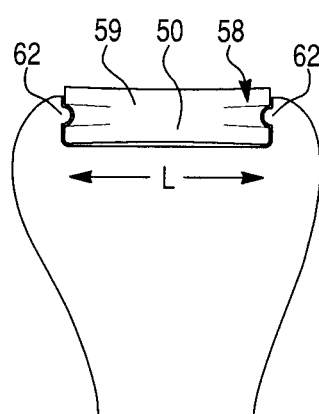
FIG. 12c is a side cross-sectional view of the prosthetic device of FIG. 12a when implanted.

As shown in the example of FIG. 12a, the prosthetic device 50 can include an implantation surface 58 and a constraint structure that includes a first projection 54 and a second projection 56 that project from the implantation surface 58 of the prosthetic device 50 in a lateral direction, as indicated by arrow L in the example of FIG. 12c, to form a recess 52. The first projection 54 and the second projection 56 can each be a single, continuous projection extending around at least a portion of the circumference of the prosthetic device 50 or include plural, discrete projections dispersed around the circumference of the prosthetic device 50. Similarly, the recess 52 can be a single, continuous channel extending around the circumference of the prosthetic device 50 or be a plurality of discrete channels dispersed around the circumference of the prosthetic device 50.

As shown in the examples of FIG. 12a-12c, the recess 52 can receive and engage a projection 62 of the bone 60 to constrain the prosthetic device 50. Providing such an engagement between the prosthetic device 50 and the bone 60 permits a practitioner to "snap" the prosthetic device 50 in place, providing confidence that the prosthetic device 50 has been implanted substantially according to a surgical plan while minimizing or preventing unwanted movement of the prosthetic device 50.

The bone 60 can have one or more bone projections 62 that engage with the prosthetic device 50. The bone projection 62 can be a single, annular bone projection 62 that extends along a portion or entirety of the circumference of the prosthetic device 50 or be plural, discrete bone projections 62 dispersed along the circumference of the prosthetic device 50.

The recess 52 also can serve as a side cement channel that is partially or fully filled with bone cement or other fixation substances during implantation of the prosthetic device 50.

Figure 13:
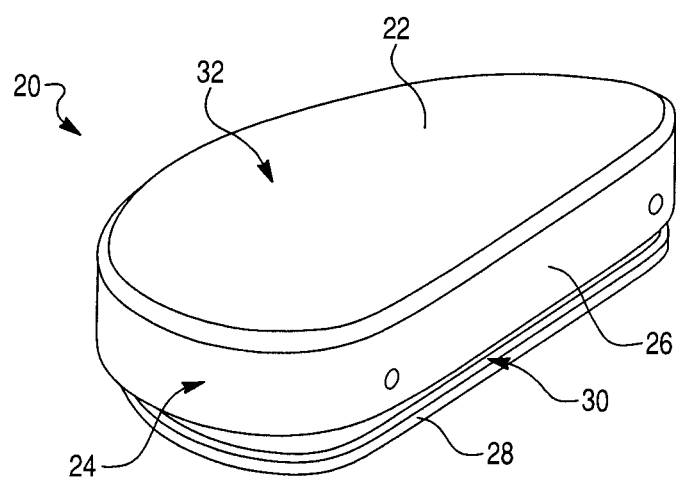
FIG. 13 is a perspective view of a prosthetic device, according to an embodiment.
Figure 14:
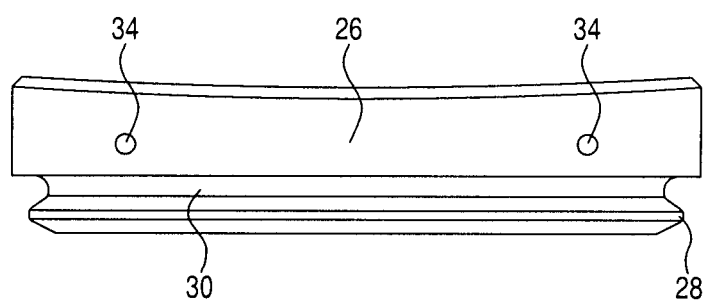
FIG. 14 is a side view of the prosthetic device of FIG. 13.

FIG. 13 shows an example of a prosthetic device 20, i.e., a tibial inlay, for implantation into a tibia, such as in the examples discussed immediately above. As shown in the example of FIG. 13, the prosthetic device 20 can include a body portion 22 for attachment to a bone and an implantation surface 24 that is configured to face the bone upon implantation of the prosthetic device 20. The prosthetic device 20 can include a constraint structure that enhances the location and positioning of the prosthetic device 20 during implantation. In the example shown in FIG. 13, the prosthetic device 20 can include a first projection 26 as a constraint structure. The first projection 26 can project in a lateral direction of the body portion 22 from the implantation surface 24 of the prosthetic device 20 so that the first projection 26 is configured to engage with a bone portion, such as a recess or projection of bone. The prosthetic device 20 may further include a second projection 28, as shown in the example of FIG. 13 and FIG. 14, which is a side view of the prosthetic device 20 shown in FIG. 13. The second projection 28 may serve as a constraint structure, alternatively or in addition to the first projection 26 because the second projection 28 may also project in a lateral direction of the body portion 22 from the implantation surface 24 of the prosthetic device 20 so that the second projection 28 is configured to engage with the prepared features of a bone, such as a recess or channel shaped to receive the second projection 28.

The second projection 28 can have a shape that is matched to the instruments used to prepare a bone surface. For example, the second projection 28 can have an edge radius that is matched to a size of an instrument used to prepare a bone surface, such as a radius of a burr, such as, for example a 6 mm burr. According to another example, the prosthetic device 20 can be configured such that all features of the prosthetic device 20 correspond to a minimal number of instruments to facilitate bone preparation. For example, the prosthetic device 20 can be configured such that a single burr, such as, for example, a 6 mm burr, can be used to prepare a bone for the prosthetic device 20.

The prosthetic device 20 can include a recess 30, as shown in the examples of FIGS. 13 and 14. The side recess 30 can be formed as a recess in the implantation surface 24 that provides a space for bone cement or another joining substance so that a relatively large fixation force can be provided between the prosthetic device 20 and the bone that the prosthetic device 20 is implanted into. Therefore, the prosthetic device 20 can have a pullout strength that is comparable to that of onlay designs. Such a side recess 30 can have a size of, for example, 0.25 to 10 mm, 0.25 to 5 mm, 0.5 to 3 mm, 1 to 2 mm, in order of preference. In the opposing direction, the same size can be applied. The shape of the form can be rectangular, circular, dovetail, cylindrical, arcuate, corrugated, or other appropriate forms, such as those that could by made by a tool such as a router.

Figure 15:
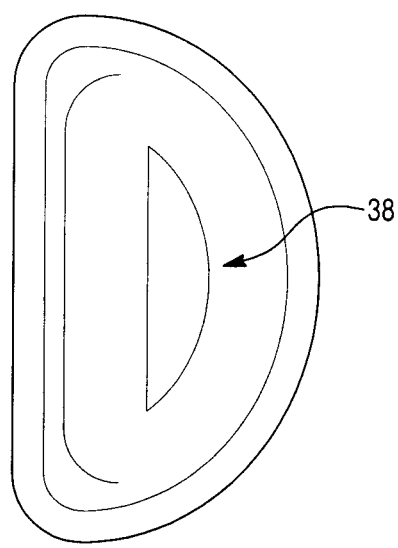
FIG. 15 is a bottom view of the prosthetic device of FIG. 13.

The prosthetic device 20 can include one or more x-ray marker pins 34 to assist in the location and positioning of the prosthetic device 20 during implantation. In addition, a bottom surface of the prosthetic device 20 can include a recess 38, as shown in the example of FIG. 15, which shows a cement pocket in the form of the letter D.

Figure 16A:
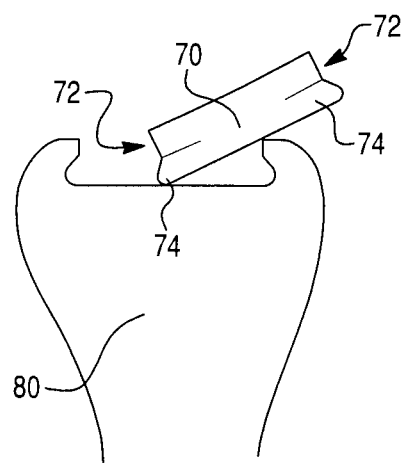
FIG. 16a is a side cross-sectional view of a prosthetic device in a first stage of implantation, according to an embodiment.
Figure 16B:
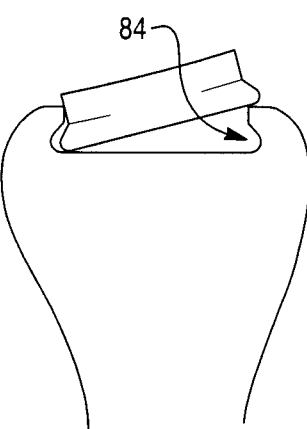
FIG. 16b is a side cross-sectional view of the prosthetic device of FIG. 16a in an advanced stage of implantation.

FIG. 16a shows a cross-sectional view of another exemplary prosthetic device 70 as the prosthetic device 70 is being implanted into a bone 80. FIG. 16b shows the prosthetic device 70 in an advanced stage of implantation into the bone 80 and FIG. 16c shows the prosthetic device 70 after implantation into the bone 80.

Figure 16C:
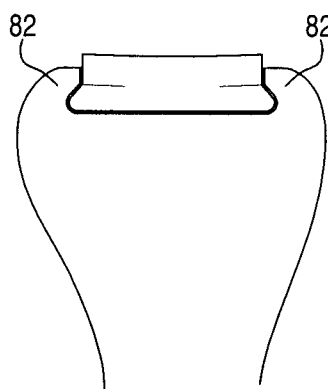
FIG. 16c is a side cross-sectional view of the prosthetic device of FIG. 16a when implanted.

In the example shown in FIGS. 16a-16c, the prosthetic device 70 includes an implantation surface 72 and a constraint structure. The constraint structure can be formed by a projection 74 projecting from the implantation surface 72 of the prosthetic device 70 to form a recess in a side of the prosthetic device 70. Such a projection 74 can be a single, continuous projection extending around at least a portion of the circumference of the prosthetic device 70 or include plural, discrete projections dispersed around the circumference of the prosthetic device 70. Such a projection 74 can engage with the bone 80 to constrain the prosthetic device 70, thus aiding in fixing the prosthetic device 70 to the bone 80 and minimizing or preventing unwanted movement of the prosthetic device 70.

The bone 80 can include a bone projection 82, which can be a single, continuous projection extending around at least a portion of a circumference of a cavity formed in the bone 80 for the prosthetic device 70 or can include a plurality of discrete projections dispersed about the circumference of the cavity in the bone 80. As shown in the examples of FIGS. 16a-16c, the projection 82 can form a recess 84, which can accommodate the projection 74 of the prosthetic device 70. Thus, the projection 74 can be configured to engage with the bone 80 at the recess 84 such that the prosthetic device 70 is constrained. Similarly, the bone forms a projection that extends into the recess formed by the projection 74.

Figure 17A:
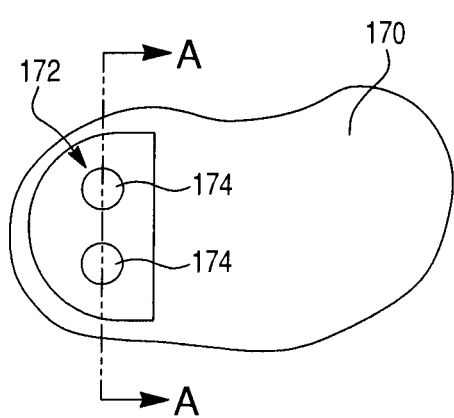
FIG. 17a is a top view of a bone with projections for projecting into recesses of a prosthetic device, according to an embodiment.
Figure 17B:
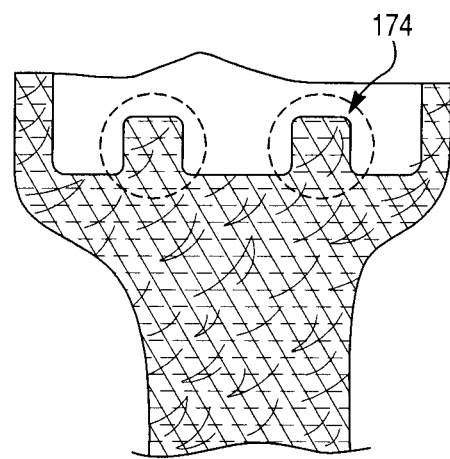
FIG. 17b is a cross sectional view taken along line A-A in FIG. 17a with a prosthetic device implanted in the pocket.

FIG. 17a shows an example of a bone 170 with a prepared pocket 172. The bone 170 includes projections 174 formed from the bone and provided within the pocket 172. As shown in FIG. 17b, which is a cross sectional view along line A-A in FIG. 17a, the projections 174 can extend vertically into the pocket 172 from a bottom surface of the prepared pocket 172. Such projections 174 can be inserted into corresponding recesses or holes in a prosthetic device to center, locate, and position the prosthetic device within the pocket 172 and to minimize or prevent unwanted movement of the prosthetic device.

Figure 18A:
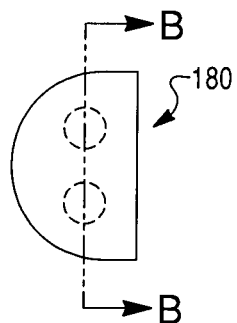
FIG. 18a is a top view of an alternative prosthetic device that implanted in pocket of the prepared bone of FIG. 17a, according to an embodiment.
Figure 18B:
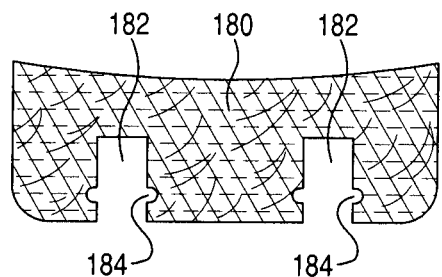

FIG. 18a is a top view of an exemplary prosthetic device 180 that can be used with the prepared bone of FIGS. 17a and 17b. As shown in FIG. 18b, which is a cross sectional view along line B-B of FIG. 18a, the prosthetic device 180 can include recesses or holes that receive the bone projections 174 of bone 170. The prosthetic device 180 can also include a channel or undercut 184 within the bone projections to provide an expansion gap or space for bone cement or other fixation substance.

Figure 19A:
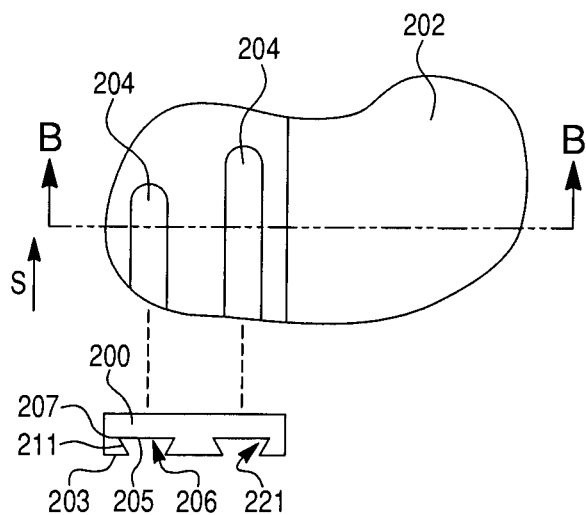
FIG. 19a is a top exploded view of a prosthetic device with recesses and bone projections, according to an embodiment.
Figure 19B:
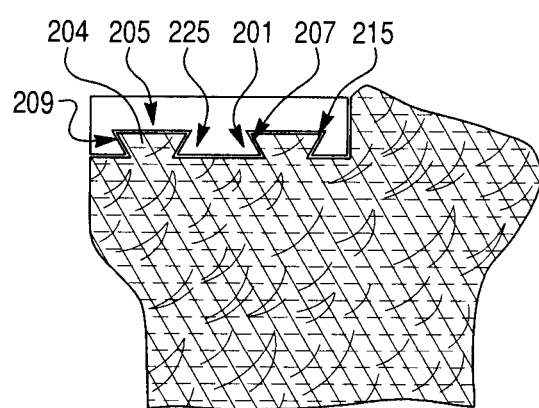
FIG. 19b is a cross sectional view taken along line B-B in FIG. 19a, with the prosthetic device implanted.

The recesses prepared in a bone and the constraint structures can also be configured to interlock with one another to constrain the prosthetic device. For example, FIG. 19a is a top view of a prosthetic device 200 and a bone 202 that has been prepared to include one or more interlock projections 204. As shown in FIG. 19b, which is a cross-sectional view along line B-B of FIG. 19a, the interlock projections 204 can extend vertically upwards from the bone 202, and the prosthetic device 200 can include one or more recesses or channels 206 configured to receive the interlock projections 204, such as by sliding the prosthetic device 200 onto the bone in the direction indicated by arrow S in FIG. 19a. The channels 206 can have a shape that is matched to the shape of the interlock projections 204, as shown in the example of FIGS. 19a and 19b. In another example, the bone projections 204 can have a dovetail shape or other shape to promote interlocking between a prosthetic device and bone.

The recesses or channels 206 in the implantation surface of the prosthetic device 200 can be configured to receive bone to constrain the body portion of the prosthetic device 200 in at least two translational degrees of freedom. For example, the recesses or channels 206 can be configured constrain the prosthetic device 200 in directions normal to the sliding direction indicated by arrow S in the example of FIG. 19a.

The recesses or channels 206 can include at least one sidewall 221 with portions for engaging bone to constrain the body portion of a prosthetic device 200 in at least two translational degrees of freedom. For example, the recesses 206 can include an inner surface 205 and a recess surface 207, with the recess surface 207 disposed between the inner surface 205 and a proximal portion 203 of an implantation surface of the prosthetic device 200 so as to form a space 209 for receiving an interlock-projection surface of the interlock projection 204 of the bone between the recess surface 207 and the inner surface 205. The recess surface 207 preferably includes a substantially planar portion 211 that extends at an obtuse angle relative to the proximal portion 203 of the implantation surface. In another example, the interlock projection 204 includes an additional interlock-projection surface that contacts an additional recess surface 225 configured to receive bone in a space between the additional recess surface 225 and the inner surface 205. In another example, the recess surface 207 can include a substantially arcuate portion. In another example, a recess or channel can include an additional recess surface configured to form a space for receiving bone between the additional recess surface and the inner surface of the recess or channel.

Figure 20:
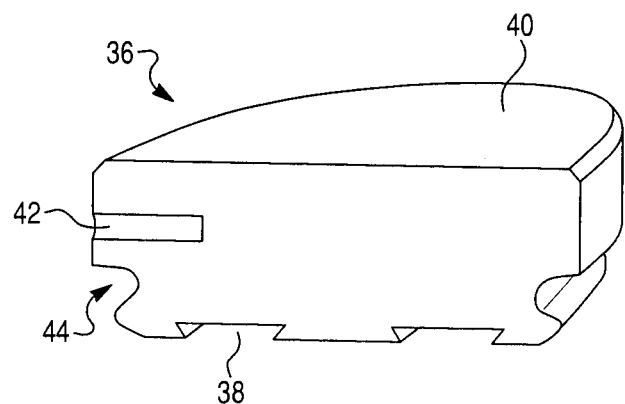

FIG. 20 shows a cross-sectional view of an exemplary prosthetic device 36 that can be used with the method shown in FIGS. 19a and 19b. As shown in FIG. 20, the prosthetic device can include one or more recesses 38 on a bottom surface of the prosthetic device 36. The recess 38 can be configured to accommodate bone cement or another joining substance during implantation of the prosthetic device 36 to enhance location and positioning of the prosthetic device 36. Thus, the recess 38 may serve as a constraint structure of the prosthetic device 36, with the bottom surface of the prosthetic device 36 serving as an implantation surface. Such a recess 38 can be partially or fully filled with bone cement or another joining substance during implantation of the prosthetic device 36.

The prosthetic device 36 can have one or more x-ray marker pins 42. Further, the prosthetic device 36 can include a recess or side cement channel 44, such as the recess discussed above, in addition to the recess 38. Such a recess 44 can be formed by one or more projections, as discussed herein.

Figure 21A:
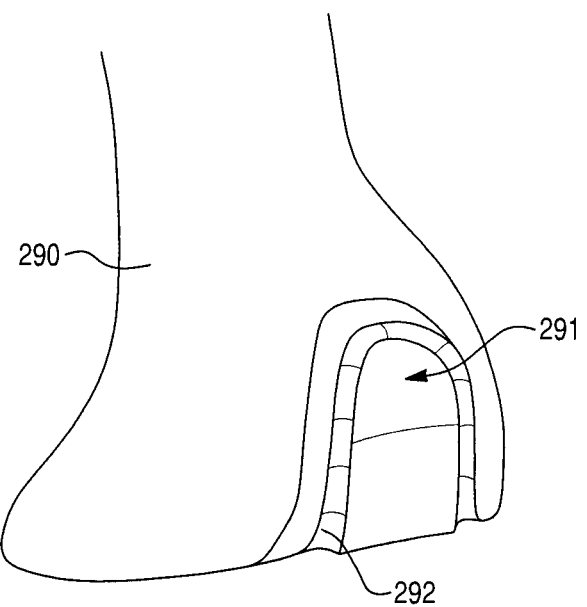
FIG. 21a is an isometric view of a femur with a pocket having a projection, according to an embodiment.

In another example, this method can also be applied to a femur. FIG. 21a shows a femur 290 that has been prepared to provide a pocket 291 to receive a prosthetic device. The pocket 291 has been selectively prepared to provide a prepared anatomical structure 292 that is configured to engage with the prosthetic device to locate and position the prosthetic device so that unwanted movement of the prosthetic device is minimized or prevented. Such a prepared anatomical structure 292 can be a projection extending from a surface of the femur 290, as shown in the example of FIG. 21a.

Figure 21B:
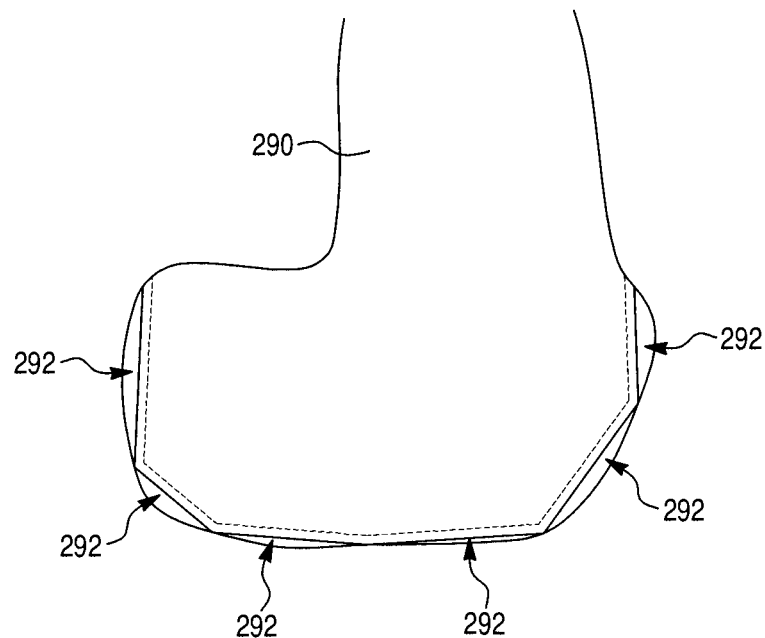
Figure 22:
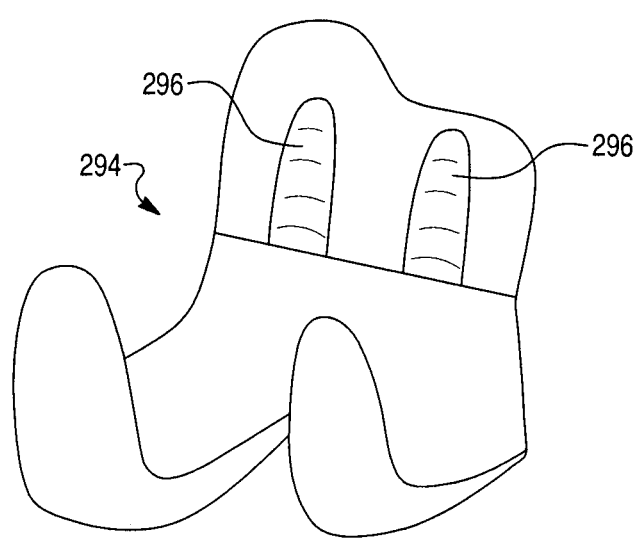

FIG. 21b shows a side cross sectional view of the femur 290 of FIG. 21a. As shown in FIG. 21b, the femur can be prepared to provide a plurality of prepared anatomical structures 292 to engage with a prosthetic device, such as the device 294 of FIG. 22, which includes one or more constraint structures, such as projections 296, to engage with the anatomical structures 292. The prosthetic device 294 can include one or more constraint structures 296, as shown in the example of FIG. 22. The constraint structure 296 can be a projection extending from a surface of the prosthetic device, as discussed in regard to the examples herein. Such projections can engage with a femur to provide a compressive force between the femur and the prosthetic device. The prosthetic device can be a total knee prosthetic device, as shown in the example of FIG. 22, or can be a unicompartmental prosthetic device or a segment of a total knee or unicompartmental prosthetic device.

The prepared anatomical structures 292 can be a plurality of recesses or channels configured to receive and engage with the features of the prosthetic device. The prepared anatomical structures 292 can be discrete structures, as shown in the example of FIG. 21b, or be a single, continuous structure. The prepared anatomical structures can extend in an anterior-posterior direction, as shown in the example of FIG. 21b.

This method can also be applied to acetabular hip prosthetic devices. In total hip arthroplasty the acetabulum receives a cup that is typically spherical in form. In an impaction technique the cup is pressed into a slightly undersized mating form. However, due to the shape of the cup inclination and/or abduction can occur, causing implantation to possibly deviate from a surgical plan.

Figure 23A:
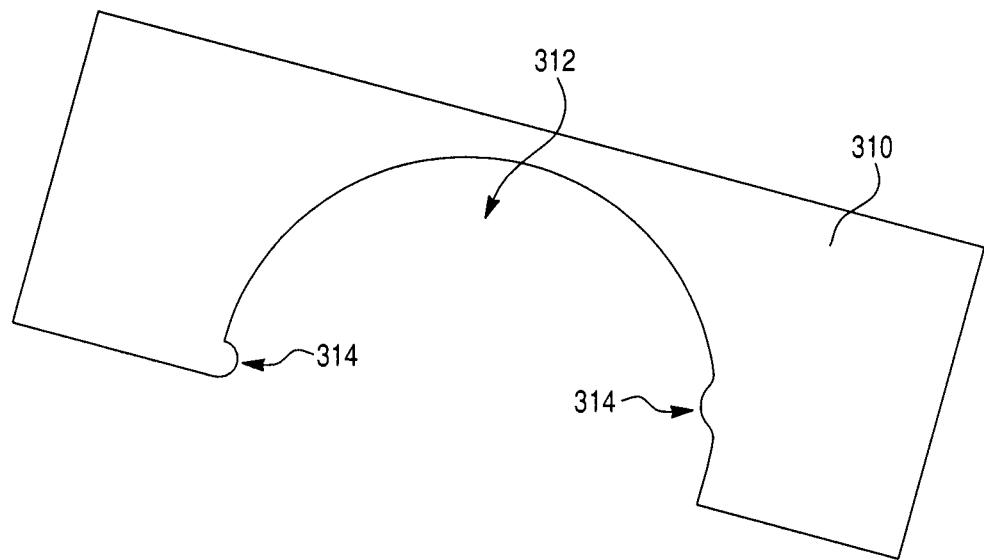
FIG. 23a is a cross sectional view of a hip bone with a pocket prepared to receive a prosthetic device, according to an embodiment.

FIG. 23a shows an example of a portion of hip bone 310 that includes a prepared pocket 312 for a prosthetic device. The hip bone 310 can be prepared to include prepared anatomical structures to engage with the prosthetic device and provide compression forces between the hip bone and the prosthetic device. For example, the prepared anatomical structures can be projections 314, as shown in the example of FIG. 23a.

Figure 23B:
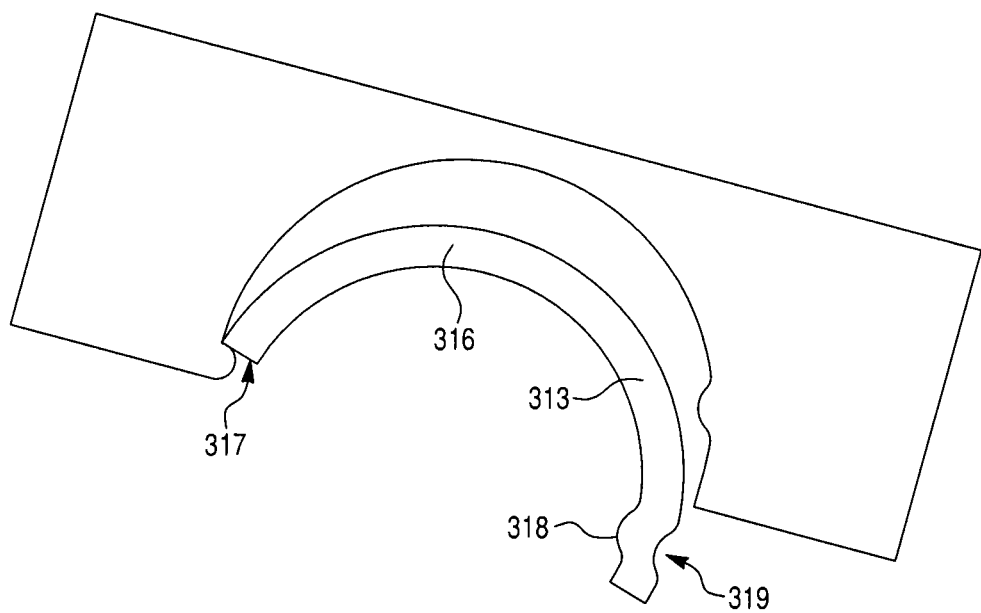
FIG. 23b is a cross sectional view of the hip bone of FIG. 23a as a prosthetic device is being inserted into the hip bone.
Figure 23C:
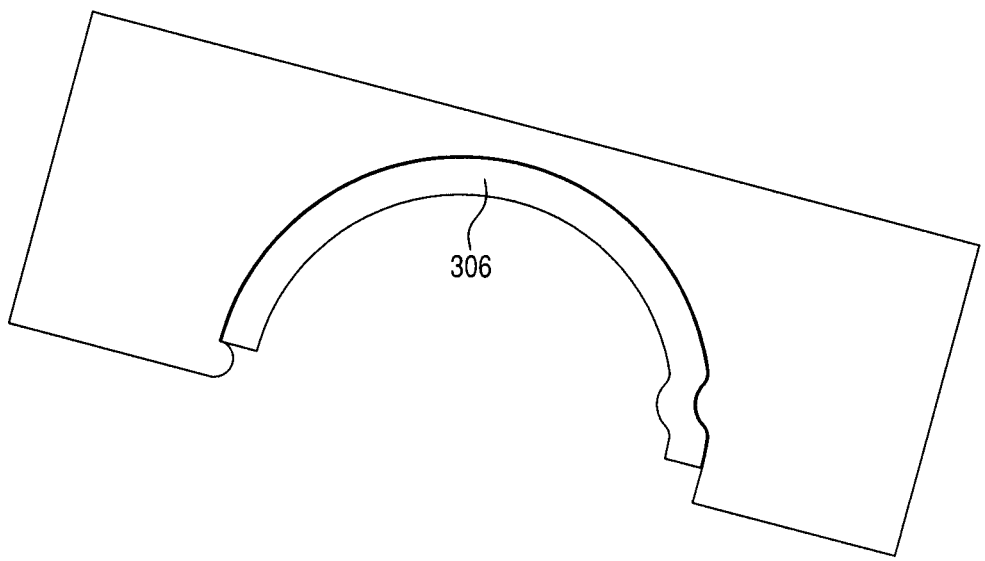
FIG. 23c is a cross sectional view of the hip bone of FIG. 23a after the prosthetic device has been implanted into the hip bone.

A prosthetic device 316 can be configured to include a constraint structure, such as a projection and/or recess 318, that engages with the prepared anatomical structures of the hip bone 310, as shown in the example of FIG. 23b, which shows the prosthetic device as it is being inserted into the pocket 312 of the hip bone 310. FIG. 23c shows the prosthetic device 316 after implantation is complete. According to an example, an end 317 of the prosthetic device 316 can engage with one or more of the projections 314 of the hip bone 310, as shown in FIGS. 23b and 23c. According to another example, the prosthetic device includes at least one recess 319 that includes a sidewall 313 with at least two portions for engaging the hip bone 310 to constrain a body portion of the acetabular cup in at least two translational degrees of freedom.

By providing the constraint structures in the prosthetic device 316 and the prepared anatomical features in the hip bone 310, the prosthetic device 316 can be located and positioned in the hip bone with minimal or no deviation from a surgical plan due to unwanted movement of the prosthetic device 316. In addition, the constraint structures in the prosthetic device 316 and the prepared anatomical features in the hip bone 310 can provide a controlled placement of the prosthetic device 316 within the hip bone 310, thus increasing confidence that implantation of the prosthetic device 316 has occurred according to a surgical plan.

Creating Bone Recess to Receive Projections from Prosthetic Device

Another implementation of the planning method includes defining the bone cutting pattern for removing a first portion of bone in the first area sufficient to seat a body portion of the prosthetic device and for removing a portion of the second portion of bone in the second area to provide a recess that is configured to receive a projection from the prosthetic device forming at least a portion of the constraint structure. For example, a constraint structure of a prosthetic device can include at least one interlock projection projecting from an implantation surface and having an interlock-projection surface configured to receive bone in a space between the interlock-projection surface and a proximal portion of the implantation surface.

Figure 24A:
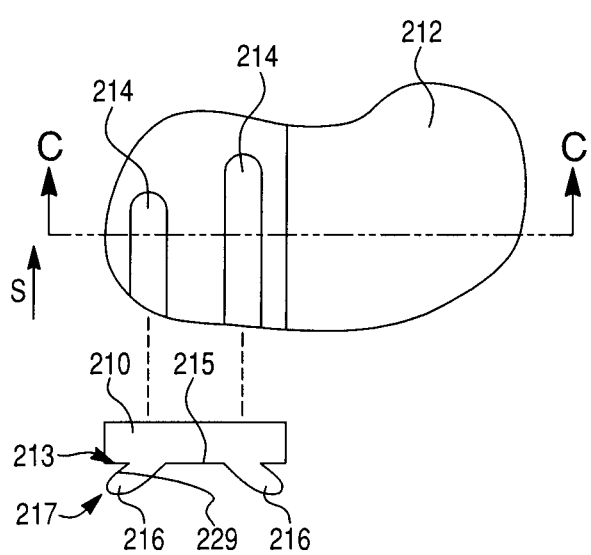
FIG. 24a is a top exploded view of a prosthetic device with projections and a bone with recesses, according to an embodiment.
Figure 24B:
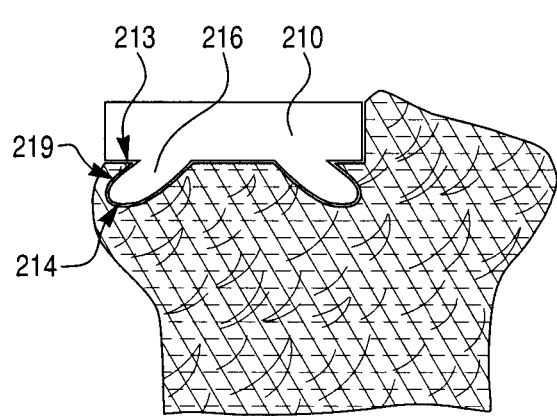
FIG. 24b is a cross sectional view taken along line C-C in FIG. 24a, with the prosthetic device implanted.

FIG. 24a is a top view of a prosthetic device 210 and a bone 212 that has been prepared to include one or more recesses or channels 214, according to another example. The prosthetic device 210 includes one or more interlock projections 216 that project from an implantation surface 215 of the prosthetic device 210. As shown in FIG. 24b, which is a cross sectional view along line C-C of FIG. 24a, the interlock projections 216 of the prosthetic device 210 can be inserted into the channels 214 of the bone 212, such as by sliding the prosthetic device 210 towards the bone 212 from a lateral side of the bone 212, as indicated by arrow S in FIG. 24a. As shown in the example of FIGS. 24a and 24b, the prosthetic device 210 can be configured to include an interlock-projection surface 217 that is configured to receive bone in a space 219 between the interlock-projection surface 219 and a proximal portion 213 of the implantation surface. The interlock-projection surface 217 can include a substantially planar portion 229 that extends over the proximal portion at an acute angle relative to the proximal portion 213 of the implantation surface. The interlock-projection surface 219 can alternatively include a substantially arcuate portion 227.

Figure 25A:
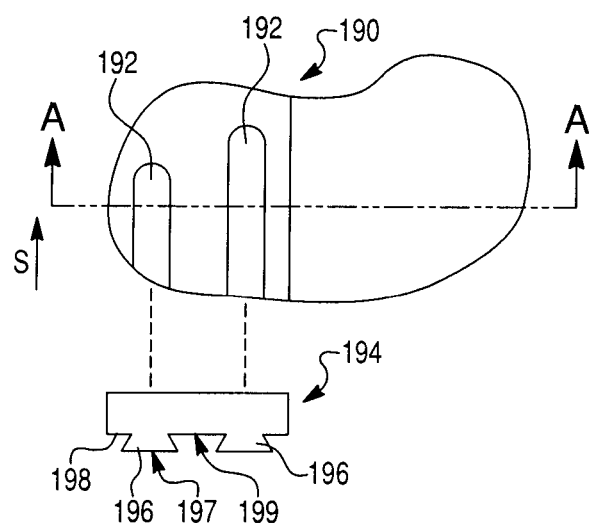
FIG. 25a is a top exploded view of a prosthetic device with projections and a bone with recesses, according to an embodiment.
Figure 25B:
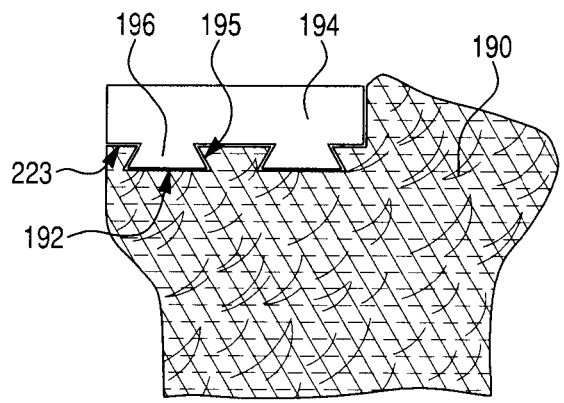
FIG. 25b is a cross sectional view taken along line A-A in FIG. 25a, with the prosthetic device implanted.

FIG. 25a is a top view of a prosthetic device 194 and a bone 190 that has been prepared to include one or more recesses or channels 192, according to another example. The prosthetic device 194 includes one or more interlock projections 196 that project from an implantation surface 198 of the prosthetic device 194. For example, the interlock projections 196 can project from a bottom side portion 223 of the implantation surface 198. As shown in FIG. 25b, which is a cross sectional view along line A-A of FIG. 25a, the interlock projections 196 of the prosthetic device 194 can be inserted into the channels 192 of the bone 190, such as by sliding the prosthetic device 194 towards the bone 190 from a lateral side of the bone 190, as indicated by arrow S in FIG. 25a. Thus, the interlock projections 196 and the channels 192 can locate and position the prosthetic device 194 relative to the bone 190 such that unwanted movement of the prosthetic device 194 is minimized or prevented. The interlock projections 196 and the channels 192 can have dovetail shapes, as shown in the examples of FIGS. 25a and 25b, or other shapes to promote interlocking between a prosthetic device and bone.

As shown in the example of FIGS. 25a and 25b, the prosthetic device 194 can be configured to include an interlock-projection surface 197 that is configured to receive bone in a space 195 between the interlock-projection surface 197 and a lower portion 199 of the implantation surface. The interlock-projection surface 197 can include a substantially planar portion that projects over and extends at an acute angle relative to the lower portion 199 of the implantation surface, as shown in the example of FIGS. 25a and 25b.

The recesses or channels in the implantation surface of the prosthetic device can be configured to receive bone to constrain the body portion of the prosthetic device in at least two translational degrees of freedom. For example, the recesses or channels can be configured constrain the prosthetic device in directions normal to the sliding direction indicated by arrow S in the examples of FIGS. 24a and 25a.

The recesses or channels and projections described above in regard to FIGS. 24a, 24b, 25a, and 25b can be used with a bone cement or other joining substance to fix a prosthetic device to a bone. Alternatively these recesses or channels and projections can be used to constrain a prosthetic device in the bone in the absence of bone cement or other adhesive substance.

Figure 26A:
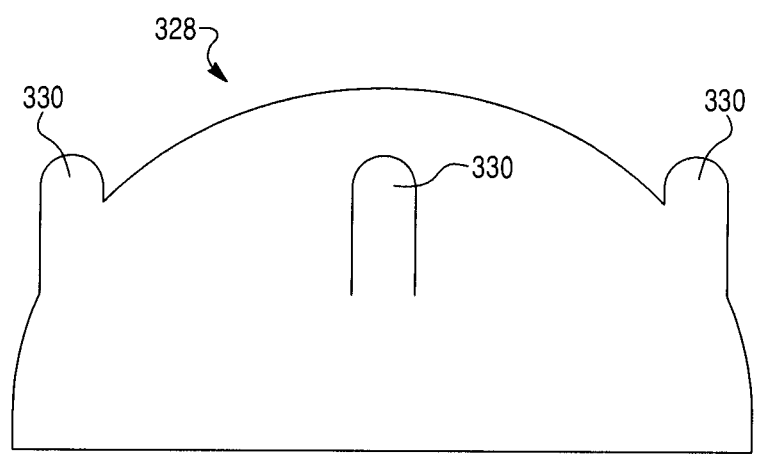
FIG. 26a is a side view of a prosthetic device, according to an embodiment.
Figure 26B:
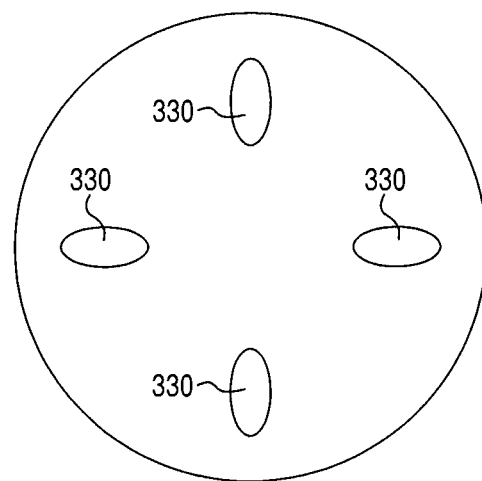

FIG. 26a shows another example of a prosthetic device 328, i.e., an acetabular cup, with a plurality of constraint structures, which can be a plurality of vertically extending projections 330, as shown in FIG. 26a and FIG. 26b. The projections shown in FIGS. 26a and 26b can be configured to engage with the prepared anatomical features of hip bone to provide desired positioning between the projections and the prepared anatomical features.

In another example, the recesses or channels can include a sidewall with at least two portions for engaging bone to constrain the body portion of a prosthetic device in at least two translational degrees of freedom. The recesses or channels can include an inner surface and a recess surface, with the recess surface disposed between the inner surface and a proximal portion of an implantation surface of the prosthetic device so as to form a space for receiving bone between the recess surface and the inner surface. In another example, the recess surface can include a substantially planar portion that extends at an obtuse angle relative to the proximal portion of the implantation surface. For example, the recess surface can be provided in the shape of a dovetail. In another example, the recess surface can include a substantially arcuate portion. In another example, a recess or channel can include an additional recess surface configured to form a space for receiving bone between the additional recess surface and the inner surface of the recess or channel.

Receiving Prosthetic Device Having Compressive Projections

To provide enhanced location and positioning of a prosthetic device in a bone, a prosthetic device can include a body portion for attachment to a bone that includes an implantation surface configured to face the bone upon implantation and a constraint structure configured to constrain the prosthetic device in the bone. The constraint structure can include at least one projection that projects from the implantation surface. Such a projection can project in a lateral direction of the body portion from the implantation surface and be configured to provide a compressive force between the prosthetic device and the bone. Such projections can create a compressive force by causing the projection to be compressed, the bone to be compressed, or both the projection and the bone to be compressed.

Figure 27:
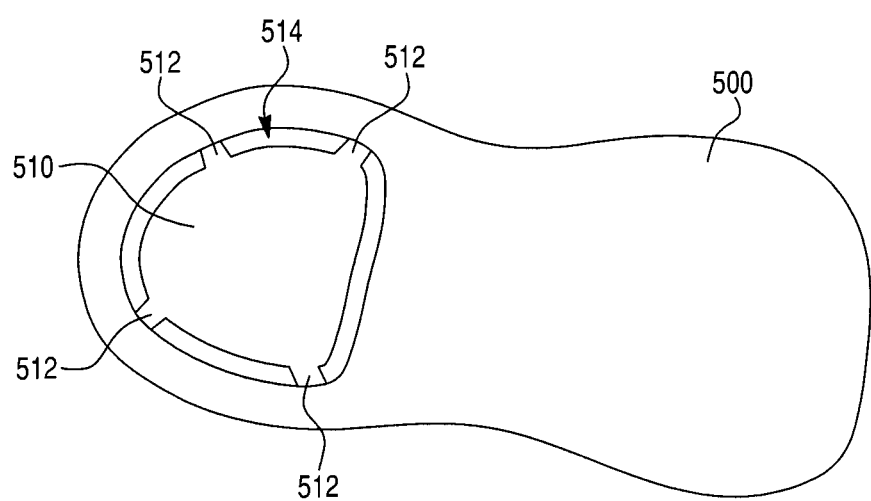
FIG. 27 is a top view of bone with a pocket and an implanted prosthetic device that includes projections, according to an embodiment.

FIG. 27 shows an example of a prosthetic device 510 implanted in a bone 500, such as a tibia. The prosthetic device 510 includes at least one constraint structure, such as a projection 512, that projects from an implantation surface 514 of the prosthetic device 510 to engage a surface of the bone 500 within a pocket prepared within the bone 500, providing a compressive force between the prosthetic device 510 and the bone 500. Such projections 512 can have different sizes and shapes, as discussed for the exemplary projections discussed herein, and can be configured to provide an interference fit with the bone 500. By providing a compressive force between the prosthetic device 510 and the bone 500, the location and positioning of the prosthetic device 510 can be aided and unwanted movement of the prosthetic device 510 can be minimized or prevented.

The projections described in the various embodiments above preferably are permanent, i.e., they remain substantially intact after the prosthetic device has been fully implanted in the pocket. However, it is not required that the projections be permanent. They instead could be temporary. For example, the projections could be utilized during a particular phase of surgery to position the prosthetic device and thereafter eliminated, e.g., crushed. As a specific example, the projections could be used to achieve initial positioning of the prosthetic device and when a surgeon drives the prosthetic device into a final implanted position, such as through an impact force, the projections could be configured to be crushed to allow the prosthetic device to move into that final implanted position.

Providing Projections for Positioning of Prosthetic Device

Figure 28A:
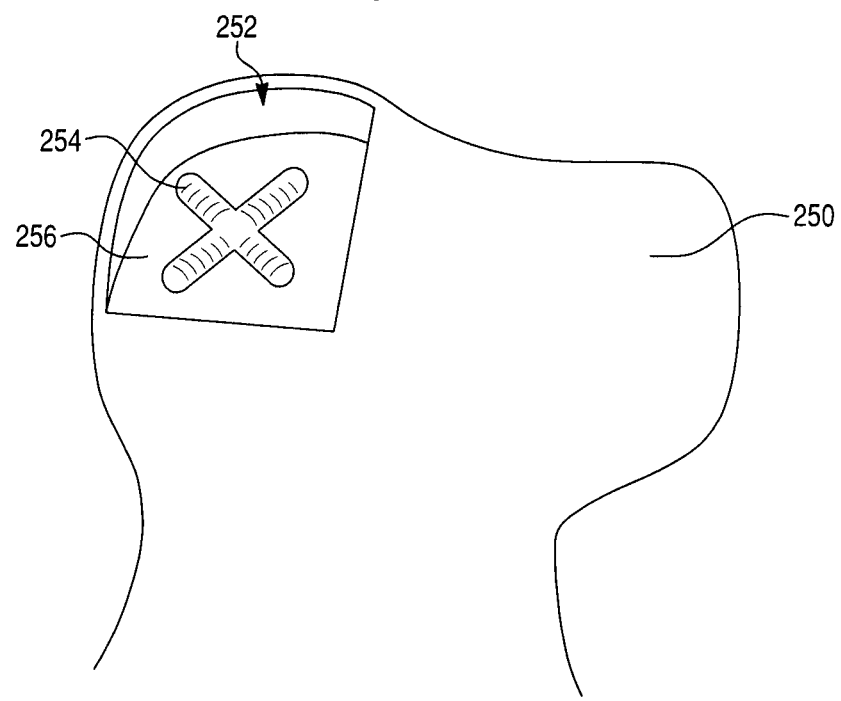
FIG. 28a is an isometric view of bone having a projection on a bottom surface of a pocket, according to an embodiment.

According to another example, a bottom surface of a pocket prepared within a bone can include a prepared anatomical structure that a prosthetic device is configured to engage such that the prosthetic device is constrained to minimize unwanted movement. As shown in the example of FIG. 28a, a pocket 252 can be prepared in a bone 250 and at least one projection 254 can be formed on a bone surface 256 of the pocket 252. The projection 254 can be prepared by selectively removing and maintaining bone tissue to provide a projection 254 that extends vertically into the pocket 252. The projection 254 can be a single projection in the shape of a cross, as shown in the example of FIG. 28a, or be one or more discrete projections with various shapes.

A projection 254 can be used to control the depth to which a prosthetic device is inserted into the pocket 252. For example, the height of the projection 254 can be designed to control the depth of the prosthetic device within the pocket 252 and/or to control an expansion gap for bone cement or other joining substance between the prosthetic device and the bone 250. Thus, the prosthetic device can sit or be placed on top of one or more projections 254 within the pocket 252. In a further example, the projections 254 can permit a practitioner to prepare the pocket 252 in less time because the top engaging surfaces of the projections 254 could be prepared with relatively high precision while the remaining portions of the bottom surface 256 could be prepared with less precision, permitting the preparation of the pocket 252 to be accomplished in less time. In addition, by providing one or more projections 254 to engage with and support a prosthetic device, any asperities that would otherwise be present in the bottom surface 256 and their effects on the location and positioning of a prosthetic device are avoided by supporting the prosthetic device above the bottom surface 256 on the projection 254.

Figure 28B:
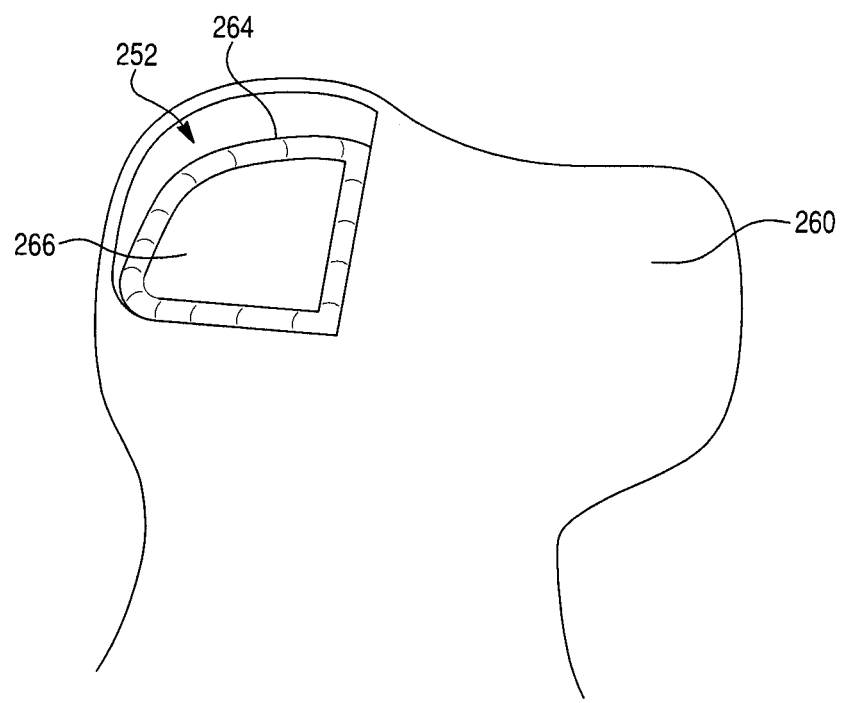
FIG. 28b is an isometric view of bone having a projection on a bottom surface of a pocket, according to an embodiment.

FIG. 28b shows another example of a pocket 262 prepared in a bone 260. The bone 260 has been selectively prepared to provide a single, continuous, annular projection 264 that extends around a circumferential perimeter of the bottom surface 266 of the pocket 262. Such a projection 264 can be used to engage with and support a prosthetic device, as discussed above in regard to the example of FIG. 28a.

Figure 28C:
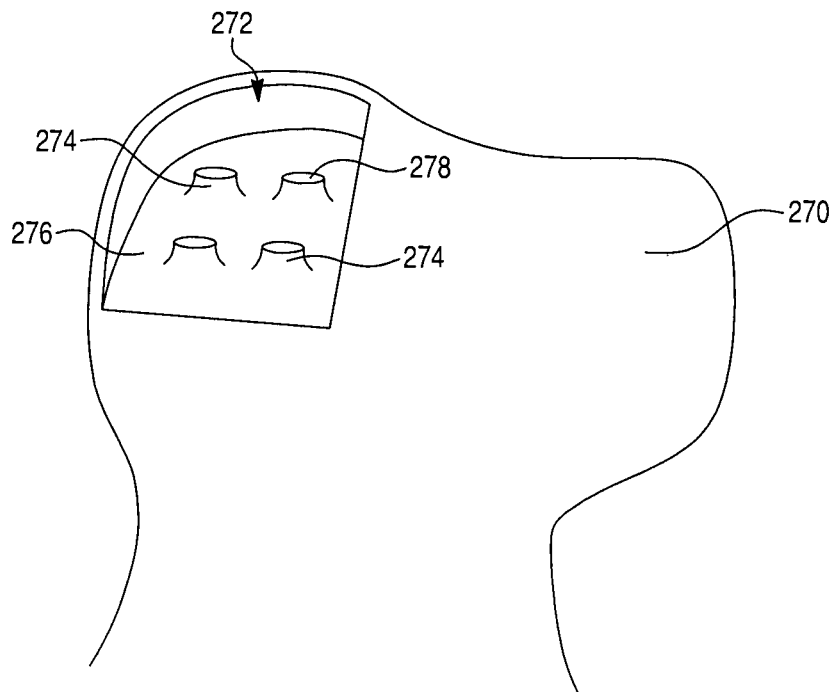
FIG. 28c is an isometric view of bone having a plurality of projections on a bottom surface of a pocket, according to an embodiment.

FIG. 28c shows another example of a pocket 272 prepared in a bone 270. The bone 270 has been selectively prepared to provide a plurality of projections 274 that extend vertically upwards from a bottom surface 276 of the pocket 272. Such projections 274 can engage with and support a prosthetic device, as discussed above in regard to the example of FIG. 28a. The projections 274 can have a top surface 278 that is substantially flat, slightly rounded, or other shapes to facilitate engagement between the prosthetic device and the projections.

Figure 29A:
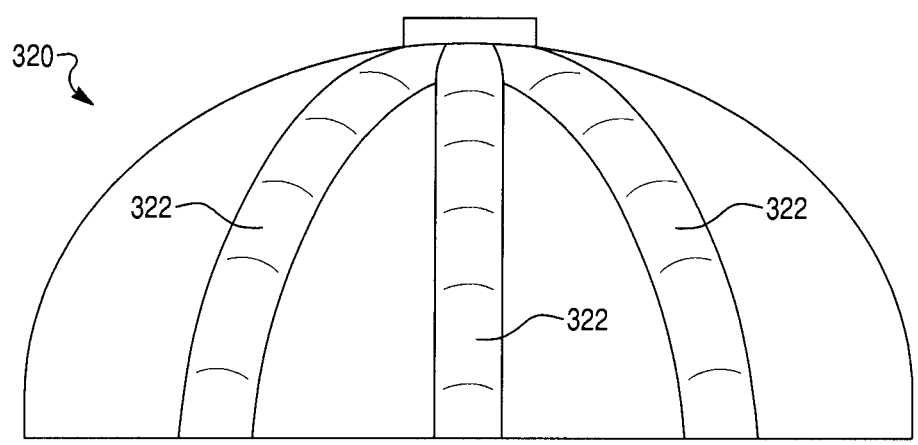
FIG. 29a is a side view of a prosthetic device with projections, according to an embodiment.
Figure 29B:
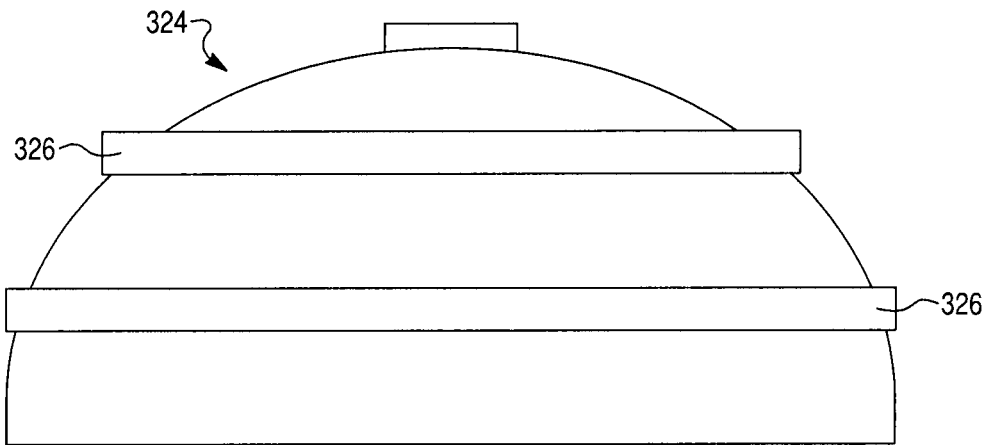
FIG. 29b is a side view of a prosthetic device with projections, according to an embodiment.

FIG. 29a shows an example of a prosthetic device 320, i.e., an acetabular cup, that includes a plurality of constraint structures. As shown in the example of FIG. 29a, the constraint structures can be a plurality of projections 322 that extend radially along the outer surface of the prosthetic device 320. Such projections can be configured to provide a desired position between the prosthetic device and the bone that the prosthetic device engages. FIG. 29b shows an example of a prosthetic device 324 that includes a plurality of horizontally oriented constraint structures, such as projections 326.

According to another example, prepared anatomical structures can be used to aid in the location and/or positioning of prosthetic devices during implantation in bone. Such prepared anatomical structures can be used to help locate and/or position one or more surfaces of a prosthetic device, such as a primary datum surface, secondary datum surface, and/or tertiary datum surface. For example, the bone preparation techniques described herein can be used to provide geometric landmarks in the pelvic region. Such geometric landmarks can assist in the implantation of a prosthetic device. For example, prepared anatomical structures can provide geometric landmarks in the pelvic region that serve as references that provide positioning information of the pelvis during implantation of a prosthetic device. In another example, selective removal or non-removal of bone can be implemented to provide prepared anatomical structures and a prosthetic device can have corresponding features, such as surfaces, projections, or recesses, that engage with or mate with the prepared anatomical structures. Both types of prepared anatomical features can provide better positioning of a prosthetic implant and visual verification of the location of a prosthetic device by surgeon, thus increasing confidence that implantation of a prosthetic device has been fully successful.

The prepared anatomical structures, such as bone projections, discussed herein can be also be used to locate or position an instrument instead of, or in addition to, a prosthetic device. For example, prepared anatomical structures, such as bone projections, can be used as visual cues when orienting and positioning a tibial baseplate that includes a keel that must be accurately inserted into a tibia. The prepared anatomical structures can also engage with or mate with instruments that guide and/or place a prosthetic device, such the tibial baseplate with a keel.

Robotic System

Figure 30:
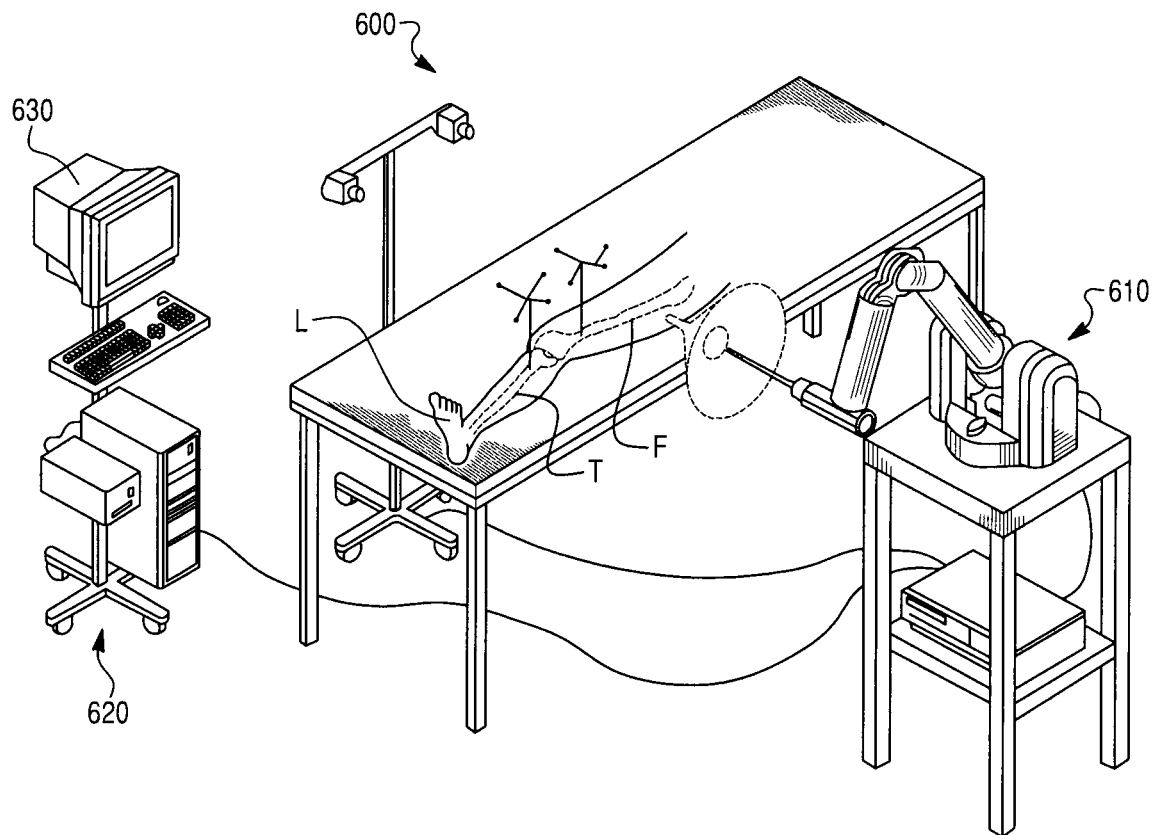
FIG. 30 is an isometric view of a robotic system, according to an embodiment.

The planning methods and prosthetic devices described herein do not require the use of a robotic system. For example, jigs or similar guiding instruments can be used to assist in the preparation of bone. However, a robotic system for preparing a bone to receive a prosthetic device can be particularly beneficial for practicing the planning methods and implanting the prosthetic devices. For example, it can increase the accuracy and precision of bone preparation and the features produced during bone preparation. FIG. 30 shows an example of a preferred haptic robotic system 600. Such a robotic system 600 is described in Published U.S. Patent Application Pub. No. 2009/0000626, which is hereby incorporated herein by reference in its entirety.

The robotic system 600 preferably includes a controllable guide structure configured to guide cutting of the bone into a shape for receiving the prosthetic device. The controllable guide structure can include, for example, a robotic arm 610. The robotic arm 610 is configured to guide a surgeon to control the resection of bone. As shown in the example of FIG. 30, the robotic arm 610 of the robotic system can be used to operate on a leg L, which includes a femur F, and a tibia T, although the robotic system 600 can be used on other bones and joints.

The robotic system 600 can include a computer 620. The computer 620 can have a computer readable medium for storing data representative of the prosthetic device. The computer 620 also can form at least part of a control system for controlling the guide structure, e.g., robotic arm 610.

The control system preferably is configured to define at least one bone-cutting pattern for (i) removing a first portion of bone in a first area sufficient to seat the body portion of the prosthetic device and (ii) at least one of removing and maintaining a second portion of bone in a second area configured to interact with the constraint structure. The control system can be configured to define the various bone-cutting patterns described above in connection with the planning methods. For example, the control system may include planning software and information about the geometry of a prosthetic device, surgical instruments used, and/or anatomy being prepared, thus providing greater surgical confidence due to the accuracy and precision of the robotic system. The software can permit manipulation of a feature plan, which can include information about the location, orientation, size, and/or shape of at least one of the prosthetic device and the anatomy being prepared so that the feature plan can be personalized for the patient but in conformance with instruments used and the prosthetic device and its features, including any mating and constraining features of the prosthetic device.

The robotic system 600 also may include a display 630 that is controlled by the control system to display information representative of the at least one bone-cutting pattern on the display.

Trauma

Figure 31A:
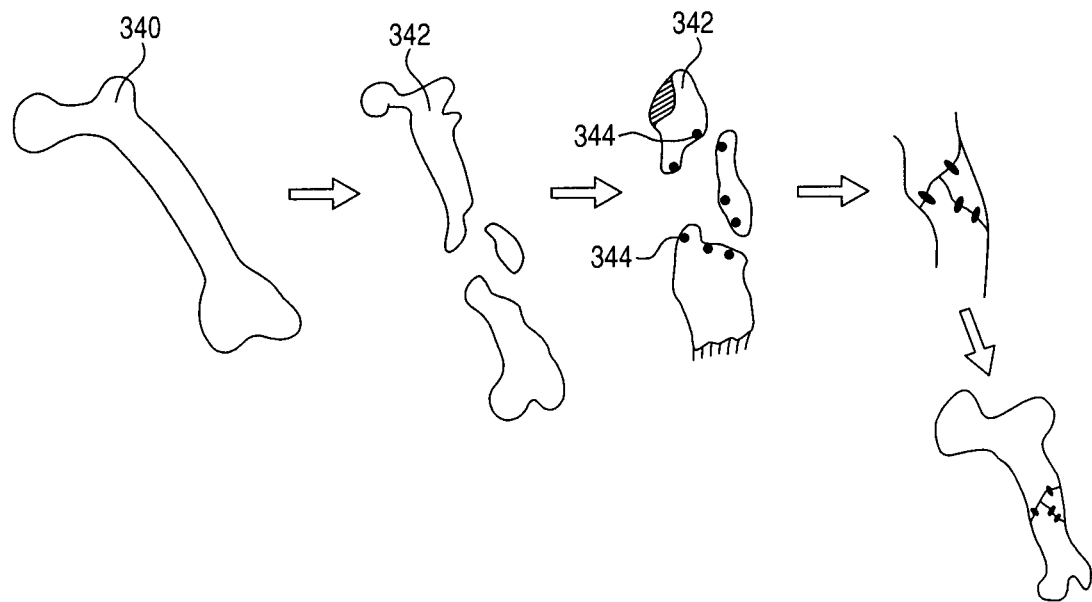
FIG. 31a is a progression of a bone that has experienced trauma and been repaired, according to an embodiment.

According to another example, the features of the examples described herein can be provided to bones that have experienced trauma, such a fracture. FIG. 31a shows a bone 340 undergoing trauma, such as one or more fractures, causing the bone 340 to be broken into multiple pieces 342. Such fractures may require surgery, including reduction and stabilization, such as when a fracture occurs mid-shaft in a femur. Such surgery requires proper alignment and orientation of the bone pieces 342.

Figure 31B:
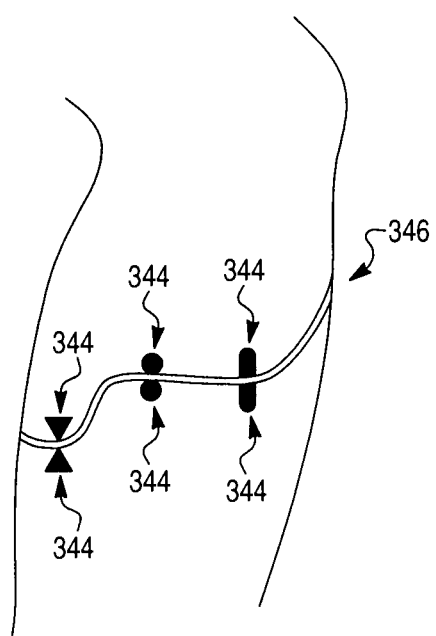
FIG. 31b is a close up of a bone fracture that has been repaired, according to an embodiment.
Figure 31C:
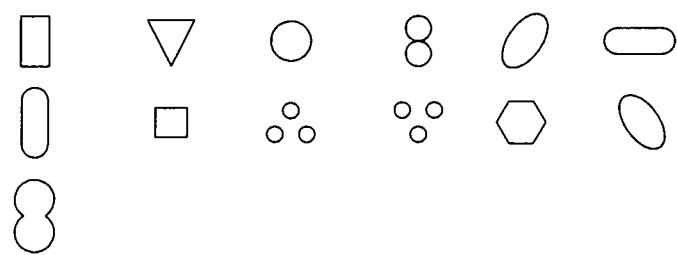
FIG. 31c is a view of various constraint structure geometries, according to an embodiment.

As shown in the example of FIG. 31a, the bone pieces 342 can be prepared to include prepared anatomical structures 344, such as a recess or channel or a projection, on each bone piece 342 to provide mating, corresponding structures. For example, a first bone piece can be provided with a recess or channel while a second bone piece that mates with the first can be provided with a projection that engages with or mates with the recess or channel of the first bone piece. Such corresponding bone pieces can be provided with a single pair of corresponding structures or a plurality of corresponding structures, as shown in the example of FIG. 31b, which shows an enlarged portion of corresponding bone pieces joined along a fracture line 346. Such structures guide joining of the bone pieces and assist in the location and positioning of the bone pieces relative to one another. In addition, the prepared anatomical structures 344 can serve only as cues to assist in the alignment and positioning of the bone pieces without acting as engagement structures. FIG. 31c shows various exemplary geometries that can be used for the prepared anatomical structures 344, or for other anatomical structures discussed herein.

Figure 32A:
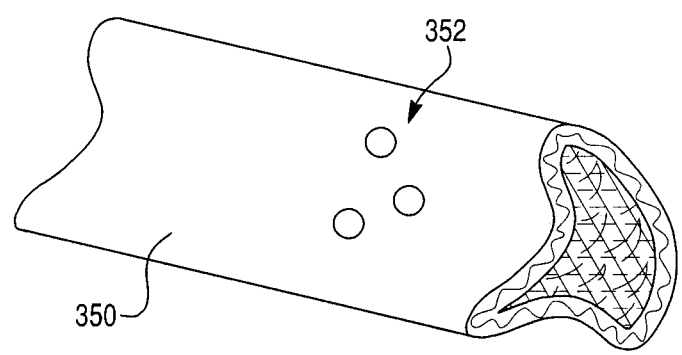
FIG. 32a is an isometric view of a bone piece prepared to engage with a hardware component, according to an embodiment.
Figure 32B:
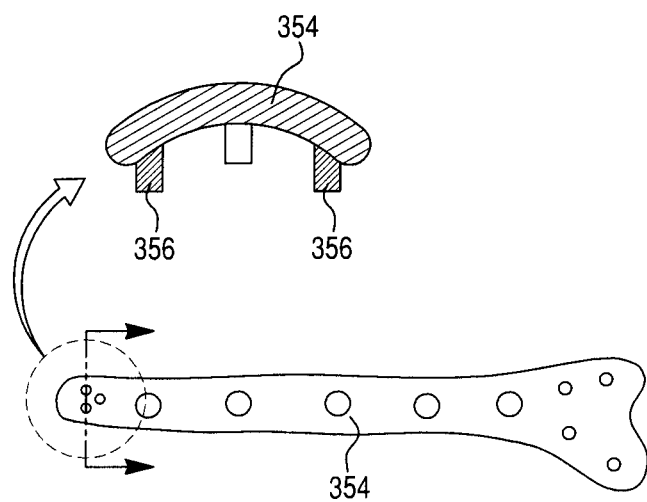
FIG. 32b includes a top view and a cross sectional view of a hardware component, according to an embodiment.

FIG. 32a shows another example of a bone piece 350 that has been fractured from a bone due to trauma. In this example, the bone piece 350 has been prepared to include prepared anatomical structures 352 to engage with a hardware component that assists in joining bone pieces and healing fractures between the bone pieces. Such prepared anatomical structures can be, for example, recesses or channels, as shown in the example of FIG. 32a, or projections extending from a surface of the bone piece 350 prepared by the selective preparation of a surface of the bone piece 350. The prepared anatomical structures 352 can be configured to engage with constraint structures of a hardware component, such as a fracture plate 354, as shown in the example of FIG. 32b. For example, the fracture plate 354 can include projections 356 that can be inserted into recesses 352 provided in the bone 350, thus guiding insertion and alignment of the fracture plate 354 relative to the bone piece 350.

Figure 33:
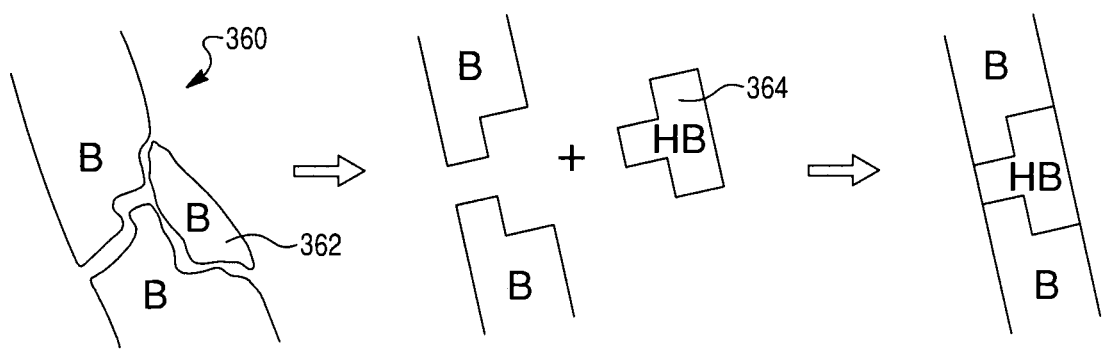
FIG. 33 is a progression of a bone that has experienced trauma and been repaired with a component that serves as an additional bone piece, according to an embodiment.
Figure 34:
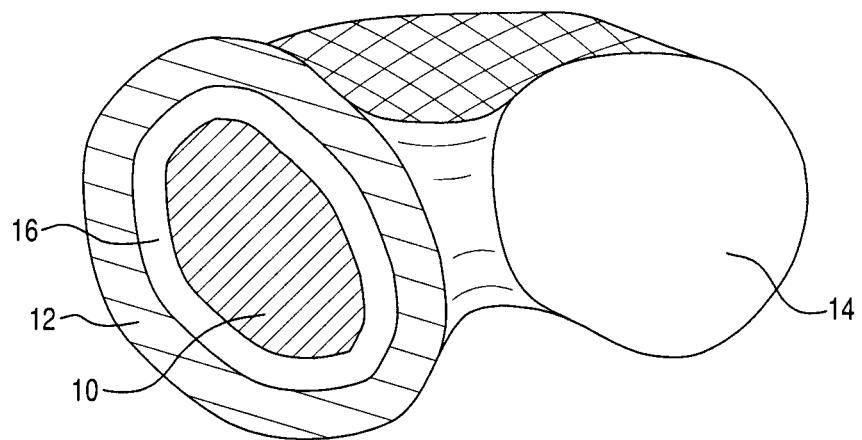
FIG. 34 is a top view of a conventional prosthetic device implanted in a tibia.

FIG. 33 shows another example of a bone 360 that has been fractured into multiple bone pieces B. However, due to surgical preparation of the bone pieces, one piece B may not be suitable for rejoining or a void may otherwise be created in the assembly of bone pieces B. An additional piece HB, such as a harvested bone piece or piece of biocompatible material may be used to replace the missing piece or void and promote healing of the trauma. The bone pieces B and additional piece HB can include prepared anatomical structures and constraint structures discussed in regard to the examples of FIGS. 31a-32b to assist in the location and positioning of the bone pieces B and the additional piece HB.

CONCLUSION

The prosthetic devices, systems, and methods described herein can be used in various bones, joints, and surgical techniques. For example, the prosthetic devices, systems, and methods described herein can be used in full or partial knee procedures, hip procedures, or shoulder procedures. In addition, the prosthetic devices, systems, and methods described herein can be used in spinal procedures, ankle procedures, elbow procedures, wrist procedures, hand procedures, foot procedures, dental procedures, such as maxilla and mandible operations, and trauma procedures.

The prosthetic devices discussed herein can be fixed to bone with a cement or other substance, such as, hydroxyapatite (HA) (collectively referred to as adhesive herein). In another example, the prosthetic devices discussed herein can be fixed to bone via a mechanical connection or interlock that does not require a cement or adhesive substance. For example, a prosthetic device can include a porous surface that has a microscopic texture that mechanically joins to a surface of a bone. The features and examples discussed above for hip prosthetic devices can also be applied to shoulder prosthetic devices because these prosthetic devices and bones have similarities.

The prosthetic devices discussed herein can be made of any suitable material, such as, for example, polymer material. The polymer could be, for example, ultra high molecular weight polyethylene (UHMWPE).

Other embodiments of the present invention will be apparent to those skilled in the art from consideration of the specification and practice of the invention disclosed herein. It is intended that the specification and examples be considered as exemplary only.

What is claimed is:

1. A system for preparing a bone to receive a prosthetic device, the system comprising:
    a controllable guide structure configured to guide a bone resection during execution of a surgical plan; and
    a control system configured to control the controllable guide structure in accordance with a bone-cutting pattern defined by the surgical plan, wherein performance of the bone resection in accordance with the bone-cutting pattern sculpts a portion of the bone into an interlock projection configured to engage with a channel of the prosthetic device.

2. The system of claim 1, wherein the interlock projection extends vertically upward from a modified surface of the bone and includes an outer surface and an angled surface, wherein the outer surface is configured to directly mate to an inner surface of the channel of the prosthetic device and the angled surface is configured to directly mate to a recess surface of the channel of the prosthetic device.

3. The system of claim 2, wherein the angled surface includes a substantially planar portion that extends at an acute angle relative to the modified surface of the bone.

4. The system of claim 1, wherein the interlock projection is configured to constrain the prosthetic device in at least two translational degrees of freedom when engaged with the channel of the prosthetic device.

5. The system of claim 1, wherein the interlock projection has a dovetail shape.

6. The system of claim 1, wherein performance of the bone resection in accordance with the bone-cutting pattern further sculpts the portion of the bone into an additional interlock projection configured to engage with an additional channel of the prosthetic device.

7. The system of claim 6, wherein the interlock projection is a first size and the additional interlock projection is a second size.

8. The system of claim 7, wherein the first size and the second size are different.

9. The system of claim 1, wherein the interlock projection has a cross shape.

10. The system of claim 1, wherein performance of the bone resection in accordance with the bone-cutting pattern further sculpts the portion of the bone into a plurality of additional interlock projections that extend vertically upward from a modified surface of the bone.

11. The system of claim 10, wherein each of the plurality of additional interlock projections comprises a top surface and a sloped surface, wherein the top surface is substantially flat and configured to directly mate to an inner surface of the prosthetic device and the sloped surface is curved and configured to directly mate to a recess surface of the prosthetic device.

12. A method, comprising:
    planning a bone-cutting pattern based on a planned installation of a prosthetic device on a bone;
    controlling a controllable guide structure to guide a cutting tool based on the bone-cutting pattern;

sculpting the bone with the cutting tool guided by the controllable guide structure, wherein sculpting the bone provides the bone with an interlock projection extending from a modified surface of the bone; and installing the prosthetic device on the bone by engaging the interlock projection with a channel of the prosthetic device.

13. The method of claim 12, wherein sculpting the bone with the cutting tool guided by the controllable guide structure forms the interlock projection such that the interlock projection extends vertically upward from the modified surface of the bone and includes an outer surface and an angled surface, wherein the outer surface is configured to mate to an inner surface of the channel of the prosthetic device and the angled surface is configured to mate to a recess surface of the channel.

14. The method of claim 13, wherein sculpting the bone with the cutting tool guided by the controllable guide structure provides the angled surface with a substantially planar portion that extends at an acute angle relative to the modified surface of the bone.

15. The method of claim 12, wherein installing the prosthetic device on the bone by engaging the interlock projection with the channel of the prosthetic device constrains the prosthetic device relative to the bone in at least two translational degrees of freedom.

16. The method of claim 12, wherein sculpting the bone with the cutting tool guided by the controllable guide structure provides the interlock projection as a dovetail shape.

17. The method of claim 12, wherein sculpting the bone with the cutting tool guided by the controllable guide structure further provides the bone with an additional interlock projection extending from the modified surface of the bone.

18. The method of claim 17, wherein sculpting the bone with the cutting tool guided by the controllable guide structure provides the interlock projection with a first size and the additional interlock projection with a second size.

19. The method of claim 12, wherein sculpting the bone with the cutting tool guided by the controllable guide structure provides the interlock projection as a cross shape.

20. A system comprising,
a prosthetic device for installation on a bone;
a robotic device configured to guide a bone resection during execution of a surgical plan; and
a control system configured to control the robotic device in accordance with a bone-cutting pattern defined by the surgical plan, the bone-cutting pattern configured to sculpt a portion of the bone into an interlock projection;
wherein the prosthetic device comprises a channel configured to receive and engage with the interlock projection such that the interlock projection prevents translational movement of the prosthetic device relative to the bone in at least two degrees of freedom.

21. The system of claim 20, wherein a shape of the channel matches a shape of the interlock projection.

22. The system of claim 20, wherein the interlock projection extends vertically upward from a modified surface of the bone.

23. The system of claim 20, wherein the interlock projection has a dovetail shape.

24. The system of claim 20, wherein performance of the bone resection in accordance with the bone-cutting pattern further sculpts the portion of the bone into an additional interlock projection configured to engage with an additional channel of the prosthetic device.

25. The system of claim 20, wherein the interlock projection is a first size and a additional interlock projection is a second size, wherein the first size and the second size are different.

26. The system of claim 20, wherein the interlock projection and the channel are cross shaped.

* * * * *